(12) United States Patent
Paul, Jr. et al.

(10) Patent No.: US 7,846,199 B2
(45) Date of Patent: Dec. 7, 2010

(54) REMODELABLE PROSTHETIC VALVE

(75) Inventors: Ram H. Paul, Jr., Bloomington, IN (US); Sean D. Chambers, Bloomington, IN (US); Chad E. Johnson, West Lafayette, IN (US)

(73) Assignees: Cook Incorporated, Bloomington, IN (US); Cook Biotech Incorporated, West Lafayette, IN (US)

( * ) Notice: Subject to any disclaimer, the term of this patent is extended or adjusted under 35 U.S.C. 154(b) by 101 days.

(21) Appl. No.: 12/273,284

(22) Filed: Nov. 18, 2008

(65) Prior Publication Data

US 2009/0138078 A1  May 28, 2009

Related U.S. Application Data

(60) Provisional application No. 60/988,981, filed on Nov. 19, 2007.

(51) Int. Cl.
*A61F 2/06* (2006.01)
(52) U.S. Cl. ..................... 623/1.24; 623/1.26
(58) Field of Classification Search ....... 623/1.24–1.26, 623/2.14, 2.18, 23.68, 2.21–2.27, 2.11; 604/9
See application file for complete search history.

(56) References Cited

U.S. PATENT DOCUMENTS

| | | | |
|---|---|---|---|
| 3,589,392 A | 6/1971 | Meyer | |
| 3,714,671 A | 2/1973 | Edwards et al. | |
| 3,755,823 A | 9/1973 | Hancock | |
| 3,903,548 A | 9/1975 | Nakib | |
| 4,106,129 A | 8/1978 | Carpentier et al. | |
| 4,178,638 A | 12/1979 | Meyer | |
| 4,218,782 A | 8/1980 | Rygg | |
| 4,222,126 A | 9/1980 | Boretos et al. | |
| 4,291,420 A | 9/1981 | Reul | |
| 4,297,749 A | 11/1981 | Davis et al. | |
| 4,339,831 A | 7/1982 | Johnson | |
| 4,343,048 A | 8/1982 | Ross et al. | |

(Continued)

FOREIGN PATENT DOCUMENTS

WO  WO 98/22158 A2  5/1998

(Continued)

OTHER PUBLICATIONS

Stephen Badylak, Ph.D., Klod Kokini, Ph.D., Bob Tullius, M.S., Abby Simmons-Byrd, R.V.T., Robert Morff, Ph.D., "Morphologic Study of Small Intestinal Submucosa as a Body Wall Repair Device," *Journal of Surgical Research*, 103, 190-202 (2002).

(Continued)

*Primary Examiner*—Alvin J. Stewart
(74) *Attorney, Agent, or Firm*—Buchanan Nipper

(57) ABSTRACT

Prosthetic medical devices with delayed valve function and in situ remodeling of a portion thereof are provided, as well as methods of manufacturing the medical devices and methods of treatment using the medical devices. The medical devices may be adapted to initially maintain a remodelable material within a body vessel in a first configuration suitable to contact the remodelable material with a body fluid contacting the remodelable material for a first time period or a second configuration adapted to regulate the flow of body fluid contacting the remodelable material. The medical devices may include a releasable holding member configured to retain the remodelable material in the first configuration.

17 Claims, 5 Drawing Sheets

U.S. PATENT DOCUMENTS

| | | | |
|---|---|---|---|
| 4,470,157 A | 9/1984 | Love | |
| 4,488,318 A | 12/1984 | Kaster | |
| 4,580,568 A | 4/1986 | Gianturco | |
| 4,605,407 A | 8/1986 | Black et al. | |
| 4,643,732 A | 2/1987 | Pietsch et al. | |
| 4,655,771 A | 4/1987 | Wallsten | |
| 4,665,906 A | 5/1987 | Jervis | |
| 4,692,164 A | 9/1987 | Dzemeshkevich et al. | |
| 4,725,274 A | 2/1988 | Lane et al. | |
| 4,728,328 A | 3/1988 | Hughes et al. | |
| 4,731,074 A | 3/1988 | Rousseau et al. | |
| 4,732,152 A | 3/1988 | Wallstén et al. | |
| 4,733,665 A | 3/1988 | Palmaz | |
| 4,759,759 A | 7/1988 | Walker et al. | |
| 4,778,461 A | 10/1988 | Pietsch et al. | |
| 4,806,595 A | 2/1989 | Noishiki et al. | |
| 4,848,343 A | 7/1989 | Wallstén et al. | |
| 4,851,000 A | 7/1989 | Gupta | |
| 4,863,467 A | 9/1989 | Bokros | |
| 4,875,480 A | 10/1989 | Imbert | |
| 4,902,508 A | 2/1990 | Badylak et al. | |
| 4,904,254 A | 2/1990 | Lane | |
| 4,935,030 A | 6/1990 | Alonso | |
| 4,950,483 A | 8/1990 | Ksander et al. | |
| 4,956,178 A | 9/1990 | Badylak et al. | |
| 5,024,841 A | 6/1991 | Chu et al. | |
| 5,026,377 A | 6/1991 | Burton et al. | |
| 5,032,128 A | 7/1991 | Alonso | |
| 5,035,706 A | 7/1991 | Giantureo et al. | |
| 5,064,435 A | 11/1991 | Porter | |
| 5,071,407 A | 12/1991 | Termin et al. | |
| 5,078,720 A | 1/1992 | Burton et al. | |
| 5,080,670 A | 1/1992 | Imamura et al. | |
| 5,110,064 A | 5/1992 | Kimura et al. | |
| 5,147,389 A | 9/1992 | Lane | |
| 5,151,105 A | 9/1992 | Kwan-Gett | |
| 5,163,951 A | 11/1992 | Pinchuk et al. | |
| 5,211,649 A | 5/1993 | Kohler et al. | |
| 5,256,418 A | 10/1993 | Kemp et al. | |
| 5,275,826 A | 1/1994 | Badylak et al. | |
| 5,281,422 A | 1/1994 | Badylak et al. | |
| 5,314,473 A * | 5/1994 | Godin | 623/23.68 |
| 5,358,518 A | 10/1994 | Camilli | |
| 5,366,473 A | 11/1994 | Winston et al. | |
| 5,370,685 A | 12/1994 | Stevens | |
| 5,375,612 A | 12/1994 | Cottenceau et al. | |
| 5,376,112 A | 12/1994 | Duran | |
| 5,376,113 A | 12/1994 | Jansen et al. | |
| 5,397,351 A | 3/1995 | Pavcnik et al. | |
| 5,411,552 A | 5/1995 | Andersen et al. | |
| 5,413,599 A | 5/1995 | Imachi et al. | |
| 5,423,887 A | 6/1995 | Love et al. | |
| 5,449,384 A | 9/1995 | Johnson | |
| 5,469,868 A | 11/1995 | Reger | |
| 5,476,471 A | 12/1995 | Shifrin et al. | |
| 5,489,298 A | 2/1996 | Love et al. | |
| 5,500,014 A | 3/1996 | Quijano et al. | |
| 5,509,930 A | 4/1996 | Love | |
| 5,545,214 A | 8/1996 | Stevens | |
| 5,554,389 A | 9/1996 | Badylak et al. | |
| 5,591,195 A | 1/1997 | Taheri et al. | |
| 5,607,465 A | 3/1997 | Camilli | |
| 5,609,598 A | 3/1997 | Laufer et al. | |
| 5,609,626 A | 3/1997 | Quijano et al. | |
| 5,649,959 A | 7/1997 | Hannam et al. | |
| 5,668,288 A | 9/1997 | Storey et al. | |
| 5,683,448 A | 11/1997 | Cragg | |
| 5,693,085 A | 12/1997 | Buirge et al. | |
| 5,711,969 A | 1/1998 | Patel et al. | |
| 5,713,953 A | 2/1998 | Vallana et al. | |
| 5,730,136 A | 3/1998 | Laufer et al. | |
| 5,733,325 A | 3/1998 | Robinson et al. | |
| 5,733,337 A | 3/1998 | Carr, Jr. et al. | |
| 5,746,766 A | 5/1998 | Edoga | |
| 5,755,782 A | 5/1998 | Love et al. | |
| 5,769,780 A | 6/1998 | Hata et al. | |
| 5,792,155 A | 8/1998 | Van Cleef et al. | |
| 5,800,408 A | 9/1998 | Strauss et al. | |
| 5,800,522 A | 9/1998 | Campbell et al. | |
| 5,810,847 A | 9/1998 | Laufer et al. | |
| 5,824,042 A | 10/1998 | Lombardi et al. | |
| 5,824,043 A | 10/1998 | Cottone, Jr. | |
| 5,824,054 A | 10/1998 | Khosravi et al. | |
| 5,824,061 A | 10/1998 | Quijano et al. | |
| 5,840,081 A | 11/1998 | Andersen et al. | |
| 5,843,167 A | 12/1998 | Dwyer et al. | |
| 5,843,171 A | 12/1998 | Campbell et al. | |
| 5,851,232 A | 12/1998 | Lois | |
| 5,855,597 A | 1/1999 | Jayaraman | |
| 5,855,601 A | 1/1999 | Bessler et al. | |
| 5,868,768 A | 2/1999 | Wicherski et al. | |
| 5,879,382 A | 3/1999 | Boneau | |
| 5,885,619 A | 3/1999 | Patel et al. | |
| 5,891,193 A | 4/1999 | Robinson et al. | |
| 5,895,419 A | 4/1999 | Tweden et al. | |
| 5,902,334 A | 5/1999 | Dwyer et al. | |
| 5,925,063 A | 7/1999 | Khosravi | |
| 5,935,161 A | 8/1999 | Robinson et al. | |
| 5,954,766 A | 9/1999 | Zadno-Azizi et al. | |
| 5,955,110 A | 9/1999 | Patel et al. | |
| 5,957,949 A | 9/1999 | Leonhardt et al. | |
| 5,961,546 A | 10/1999 | Robinson et al. | |
| 5,968,096 A | 10/1999 | Whitson et al. | |
| 5,980,565 A | 11/1999 | Jayaraman | |
| 5,993,844 A | 11/1999 | Abraham et al. | |
| 5,997,573 A | 12/1999 | Quijano et al. | |
| 6,004,347 A | 12/1999 | McNamara et al. | |
| 6,015,431 A | 1/2000 | Thornton et al. | |
| 6,022,374 A | 2/2000 | Imran | |
| 6,033,398 A | 3/2000 | Farley et al. | |
| 6,036,687 A | 3/2000 | Laufer et al. | |
| 6,099,567 A | 8/2000 | Badylak et al. | |
| 6,110,201 A | 8/2000 | Quijano et al. | |
| 6,110,212 A | 8/2000 | Gregory | |
| 6,117,979 A | 9/2000 | Hendriks et al. | |
| 6,126,686 A | 10/2000 | Badylak et al. | |
| 6,136,025 A | 10/2000 | Barbut et al. | |
| 6,139,575 A | 10/2000 | Shu et al. | |
| 6,143,022 A | 11/2000 | Shull et al. | |
| 6,149,660 A | 11/2000 | Laufer et al. | |
| 6,162,245 A | 12/2000 | Jayaraman | |
| 6,165,218 A * | 12/2000 | Husson et al. | 623/17.11 |
| 6,168,614 B1 | 1/2001 | Andersen et al. | |
| 6,176,875 B1 | 1/2001 | Lenker et al. | |
| 6,187,036 B1 | 2/2001 | Shaolian et al. | |
| 6,200,336 B1 | 3/2001 | Pavcnik et al. | |
| 6,206,931 B1 | 3/2001 | Cook et al. | |
| 6,221,091 B1 | 4/2001 | Khosravi | |
| 6,231,507 B1 | 5/2001 | Zikorus et al. | |
| 6,241,763 B1 | 6/2001 | Drasler et al. | |
| 6,245,102 B1 | 6/2001 | Jayaraman | |
| 6,254,564 B1 | 7/2001 | Wilk et al. | |
| 6,269,819 B1 | 8/2001 | Oz et al. | |
| 6,280,467 B1 | 8/2001 | Leonhardt | |
| 6,287,334 B1 * | 9/2001 | Moll et al. | 623/1.24 |
| 6,287,335 B1 | 9/2001 | Drasler et al. | |
| 6,287,339 B1 | 9/2001 | Vazquez et al. | |
| 6,290,721 B1 | 9/2001 | Heath | |
| 6,293,968 B1 | 9/2001 | Taheri | |
| 6,296,661 B1 | 10/2001 | Davila et al. | |
| 6,299,636 B1 | 10/2001 | Schmitt et al. | |
| 6,299,637 B1 * | 10/2001 | Shaolian et al. | 623/1.24 |
| 6,315,791 B1 | 11/2001 | Gingras et al. | |
| 6,315,793 B1 | 11/2001 | Bokros et al. | |

| | | | | | | |
|---|---|---|---|---|---|---|
| 6,334,868 B1 | 1/2002 | Ham | | 2001/0039450 A1 | 11/2001 | Pavcnik et al. |
| 6,334,872 B1 | 1/2002 | Termin et al. | | 2001/0044654 A1 | 11/2001 | Chen et al. |
| 6,334,873 B1 | 1/2002 | Lane et al. | | 2001/0047198 A1 | 11/2001 | Drasler et al. |
| 6,342,070 B1 | 1/2002 | Nguyen-Thien-Nhon et al. | | 2002/0002401 A1 | 1/2002 | McGuckin et al. |
| 6,344,052 B1 | 2/2002 | Greenan et al. | | 2002/0032481 A1 | 3/2002 | Gabbay |
| 6,361,496 B1 | 3/2002 | Zikorus et al. | | 2002/0055772 A1 | 5/2002 | McGuckin et al. |
| 6,375,989 B1 | 4/2002 | Badylak et al. | | 2002/0077696 A1 | 6/2002 | Zadno-Azizi et al. |
| 6,379,710 B1 | 4/2002 | Badylak | | 2002/0095209 A1 | 7/2002 | Zadno-Azizi et al. |
| 6,425,916 B1 | 7/2002 | Garrison et al. | | 2002/0099439 A1 | 7/2002 | Schwartz et al. |
| 6,440,164 B1 | 8/2002 | DiMatteo et al. | | 2002/0107565 A1 | 8/2002 | Greenhalgh |
| 6,443,988 B2 * | 9/2002 | Felt et al. ............... 623/17.12 | | 2002/0123800 A1 | 9/2002 | Taheri |
| 6,444,229 B2 | 9/2002 | Voytik-Harbin et al. | | 2002/0138135 A1 | 9/2002 | Duerig et al. |
| 6,451,051 B2 | 9/2002 | Drasler et al. | | 2002/0151968 A1 | 10/2002 | Zilla et al. |
| 6,454,799 B1 | 9/2002 | Schreck | | 2002/0151970 A1 | 10/2002 | Garrison et al. |
| 6,458,153 B1 * | 10/2002 | Bailey et al. ............... 623/1.24 | | 2002/0177894 A1 | 11/2002 | Acosta et al. |
| 6,478,819 B2 * | 11/2002 | Moe ............................ 623/2.18 | | 2002/0188348 A1 | 12/2002 | DiMatteo et al. |
| 6,494,909 B2 * | 12/2002 | Greenhalgh ................ 623/1.24 | | 2003/0018358 A1 | 1/2003 | Saadat |
| 6,503,272 B2 * | 1/2003 | Duerig et al. ............. 623/1.24 | | 2003/0023300 A1 | 1/2003 | Bailey et al. |
| 6,508,833 B2 * | 1/2003 | Pavcnik et al. ............ 623/1.15 | | 2003/0023303 A1 | 1/2003 | Palmaz et al. |
| 6,527,800 B1 | 3/2003 | McGuckin, Jr. et al. | | 2003/0036795 A1 | 2/2003 | Andersen et al. |
| 6,530,952 B2 * | 3/2003 | Vesely ........................ 623/2.18 | | 2003/0040792 A1 | 2/2003 | Gabbay |
| 6,558,429 B2 * | 5/2003 | Taylor ...................... 623/23.68 | | 2003/0051735 A1 | 3/2003 | Pavcnik et al. |
| 6,562,068 B2 | 5/2003 | Drasler et al. | | 2003/0055492 A1 | 3/2003 | Shaolian et al. |
| 6,562,069 B2 | 5/2003 | Cai et al. | | 2003/0055495 A1 | 3/2003 | Pease et al. |
| 6,572,650 B1 | 6/2003 | Abraham et al. | | 2003/0055496 A1 | 3/2003 | Cai et al. |
| 6,575,971 B2 | 6/2003 | Hauck et al. | | 2003/0060875 A1 | 3/2003 | Wittens |
| 6,579,538 B1 | 6/2003 | Spievack | | 2003/0083741 A1 | 5/2003 | Woo et al. |
| 6,582,462 B1 | 6/2003 | Andersen et al. | | 2003/0093071 A1 | 5/2003 | Hauck et al. |
| 6,585,761 B2 | 7/2003 | Taheri | | 2003/0114913 A1 | 6/2003 | Spenser et al. |
| 6,602,286 B1 | 8/2003 | Strecker | | 2003/0125795 A1 | 7/2003 | Pavcnik et al. |
| 6,605,112 B1 | 8/2003 | Moll et al. | | 2003/0130726 A1 | 7/2003 | Thorpe et al. |
| 6,632,243 B1 | 10/2003 | Zadno-Azizi et al. | | 2003/0130727 A1 | 7/2003 | Drasler et al. |
| 6,652,578 B2 | 11/2003 | Bailey et al. | | 2003/0149477 A1 | 8/2003 | Gabbay |
| 6,666,886 B1 | 12/2003 | Tranquillo et al. | | 2003/0171802 A1 | 9/2003 | Wilder et al. |
| 6,669,724 B2 * | 12/2003 | Park et al. .................. 623/1.24 | | 2003/0171824 A1 | 9/2003 | Abraham et al. |
| 6,676,698 B2 | 1/2004 | McGuckin, Jr. et al. | | 2003/0175410 A1 | 9/2003 | Campbell et al. |
| 6,685,739 B2 | 2/2004 | DiMatteo et al. | | 2003/0191525 A1 | 10/2003 | Thornton |
| 6,689,161 B2 | 2/2004 | Chen et al. | | 2003/0191528 A1 | 10/2003 | Quijano et al. |
| 6,695,833 B1 | 2/2004 | Frantzen | | 2003/0195618 A1 | 10/2003 | Abraham et al. |
| 6,695,878 B2 | 2/2004 | McGuckin, Jr. et al. | | 2003/0199971 A1 | 10/2003 | Tower et al. |
| 6,705,585 B1 | 3/2004 | Roy | | 2003/0199972 A1 | 10/2003 | Zadno-Azizi et al. |
| 6,716,241 B2 | 4/2004 | Wilder et al. | | 2003/0208261 A1 * | 11/2003 | Thorpe et al. ............... 623/1.16 |
| 6,730,118 B2 | 5/2004 | Spenser et al. | | 2003/0209835 A1 | 11/2003 | Chun et al. |
| 6,752,828 B2 * | 6/2004 | Thornton ................... 623/1.24 | | 2003/0212452 A1 * | 11/2003 | Zadno-Azizi et al. ....... 623/1.24 |
| 6,764,510 B2 | 7/2004 | Vidlund et al. | | 2003/0216679 A1 * | 11/2003 | Wolf et al. ..................... 604/8 |
| 6,830,585 B1 | 12/2004 | Artof et al. | | 2003/0216764 A1 | 11/2003 | Tu et al. |
| 6,840,957 B2 | 1/2005 | DiMatteo et al. | | 2003/0225447 A1 | 12/2003 | Majercak et al. |
| 6,875,231 B2 | 4/2005 | Anduiza et al. | | 2003/0229393 A1 | 12/2003 | Kutryk et al. |
| 6,951,571 B1 * | 10/2005 | Srivastava .................. 623/1.24 | | 2003/0236568 A1 | 12/2003 | Hojeibane et al. |
| 6,979,350 B2 * | 12/2005 | Moll et al. .................. 623/1.24 | | 2004/0002719 A1 | 1/2004 | Oz et al. |
| 7,125,418 B2 * | 10/2006 | Duran et al. ............... 623/1.24 | | 2004/0015230 A1 | 1/2004 | Moll et al. |
| 7,128,759 B2 * | 10/2006 | Osborne et al. ............ 623/1.24 | | 2004/0019374 A1 | 1/2004 | Hojeibane et al. |
| 7,153,324 B2 * | 12/2006 | Case et al. .................. 623/1.24 | | 2004/0024447 A1 | 2/2004 | Haverich |
| 7,159,593 B2 | 1/2007 | McCarthy et al. | | 2004/0024452 A1 | 2/2004 | Kruse et al. |
| 7,175,656 B2 * | 2/2007 | Khairkhahan ............. 623/1.26 | | 2004/0030249 A1 | 2/2004 | Willis |
| 7,182,788 B2 * | 2/2007 | Jung et al. ................ 623/23.68 | | 2004/0034408 A1 | 2/2004 | Majercak et al. |
| 7,201,772 B2 * | 4/2007 | Schwammenthal et al. 623/2.18 | | 2004/0039436 A1 | 2/2004 | Spenser et al. |
| 7,452,371 B2 * | 11/2008 | Pavcnik et al. ............ 623/1.24 | | 2004/0049266 A1 | 3/2004 | Anduiza et al. |
| 7,458,987 B2 * | 12/2008 | Case et al. .................. 623/1.24 | | 2004/0054396 A1 | 3/2004 | Hartley et al. |
| 7,547,322 B2 * | 6/2009 | Sarac et al. ................. 623/1.24 | | 2004/0059411 A1 | 3/2004 | Strecker |
| 7,566,343 B2 * | 7/2009 | Jenson et al. ............... 623/2.12 | | 2004/0092858 A1 | 5/2004 | Wilson et al. |
| 7,618,447 B2 * | 11/2009 | Case et al. .................. 623/1.26 | | 2004/0093070 A1 | 5/2004 | Hojeibane et al. |
| 7,628,803 B2 * | 12/2009 | Pavcnik et al. ............ 623/1.24 | | 2004/0098098 A1 | 5/2004 | McGuckin et al. |
| 7,678,144 B2 * | 3/2010 | Bailey et al. ............... 623/2.16 | | 2004/0098112 A1 | 5/2004 | DiMatteo et al. |
| 7,686,844 B2 * | 3/2010 | Case et al. .................. 623/1.24 | | 2004/0106976 A1 | 6/2004 | Bailey et al. |
| 7,749,245 B2 * | 7/2010 | Cohn et al. ................. 606/200 | | 2004/0117019 A1 * | 6/2004 | Trieu et al. ............... 623/17.11 |
| 7,753,949 B2 * | 7/2010 | Lamphere et al. .......... 623/1.26 | | 2004/0137042 A1 | 7/2004 | Hiles et al. |
| 2001/0005787 A1 | 6/2001 | Oz et al. | | 2004/0137618 A1 | 7/2004 | Chen et al. |
| 2001/0007956 A1 | 7/2001 | Letac et al. | | 2004/0138684 A1 | 7/2004 | Eton |
| 2001/0010017 A1 | 7/2001 | Letac et al. | | 2004/0167619 A1 | 8/2004 | Case et al. |
| 2001/0011187 A1 | 8/2001 | Pavcnik et al. | | 2004/0180042 A1 | 9/2004 | Cook et al. |
| 2001/0011189 A1 | 8/2001 | Drasler et al. | | 2004/0186558 A1 | 9/2004 | Pavcnik et al. |
| 2001/0021872 A1 | 9/2001 | Bailey et al. | | 2004/0193253 A1 | 9/2004 | Thorpe et al. |

| | | | |
|---|---|---|---|
| 2004/0199183 A1 | 10/2004 | Oz et al. | |
| 2004/0210301 A1 | 10/2004 | Obermiller | |
| 2004/0210306 A1 | 10/2004 | Quijano et al. | |
| 2004/0210307 A1 | 10/2004 | Khairkhahan | |
| 2004/0215339 A1 | 10/2004 | Drasler et al. | |
| 2004/0225352 A1 | 11/2004 | Osborne et al. | |
| 2004/0236411 A1* | 11/2004 | Sarac et al. | 623/1.26 |
| 2004/0243222 A1 | 12/2004 | Osborne et al. | |
| 2004/0254636 A1 | 12/2004 | Flagle et al. | |
| 2004/0260389 A1 | 12/2004 | Case et al. | |
| 2004/0260390 A1 | 12/2004 | Sarac et al. | |
| 2005/0027348 A1 | 2/2005 | Case et al. | |
| 2005/0049692 A1 | 3/2005 | Numamoto et al. | |
| 2005/0065594 A1 | 3/2005 | DiMatteo et al. | |
| 2005/0075720 A1* | 4/2005 | Nguyen et al. | 623/1.26 |
| 2005/0096736 A1* | 5/2005 | Osse et al. | 623/1.26 |
| 2005/0137690 A1* | 6/2005 | Salahieh et al. | 623/2.11 |
| 2005/0203616 A1* | 9/2005 | Cribier | 623/2.11 |
| 2005/0216085 A1* | 9/2005 | Michelson | 623/17.11 |
| 2005/0222661 A1 | 10/2005 | Case et al. | |
| 2006/0009841 A1* | 1/2006 | McGuckin et al. | 623/2.38 |
| 2006/0058889 A1* | 3/2006 | Case et al. | 623/23.68 |
| 2007/0154515 A1 | 7/2007 | Johnson et al. | |
| 2007/0191861 A1* | 8/2007 | Allard et al. | 606/99 |
| 2007/0198025 A1* | 8/2007 | Trieu et al. | 606/105 |
| 2009/0112309 A1* | 4/2009 | Jaramillo et al. | 623/1.26 |
| 2009/0216310 A1* | 8/2009 | Straubinger et al. | 623/1.15 |
| 2010/0114305 A1* | 5/2010 | Kang et al. | 623/2.1 |
| 2010/0114327 A1* | 5/2010 | Sobrino-Serrano | 623/23.68 |

FOREIGN PATENT DOCUMENTS

| | | |
|---|---|---|
| WO | WO 98/25636 A1 | 6/1998 |
| WO | WO 98/25637 A1 | 6/1998 |
| WO | WO 98/26291 A1 | 6/1998 |
| WO | WO 00/38590 A1 | 7/2000 |
| WO | WO 01/66161 A1 | 9/2001 |
| WO | WO 02/100245 A2 | 12/2002 |

OTHER PUBLICATIONS

Elias Brountzos, MD, Dusan Pavcnik, MD, PhD, Hans A. Timmermans, BFA, Christopher Corless, MD, PhD, Barry T. Uchida, BS, Edith S. Nihsen, BA, Manabu Nakata, MD, PhD, Maria Schoder, MD, John A. Kaufman, MD, Frederick S. Keller, MD, Josef Rösch, MD, "Remodeling of Suspended Small Intestinal Submucosa Venous Valve: An Experimental Study in Sheep to Assess the Host Cells' Origin," *J. Vasc. Interv. Radiol* vol. 14, No. 3, 349-356 (2003).

Zhonggang Feng, PhD., Toyoaki Matsumoto, Takao Nakamura, PhD., "Measurements of the mechanical properties of contracted collagen gels populated with rat fibroblasts or cardiomyocytes," *The Japanese Society for Artificial Organs*, 192-196 (2003).

Stephen S. Kim, Satoshi Kaihara, Mark S. Benvenuto, Byung-Soo Kim, David J. Mooney, Joseph P. Vacanti, "Small Intestinal Submucosa as a Small-Caliber Venous Graft: A Novel Model for Hepatocyte Transplantation on Synthetic Biodegradable Polymer Scaffolds with Direct Access to the Portal Venous System," *Journal of Pediatric Surgery*, Vo. 34, No. 1 124-128 (1999).

Fedor Lurie, MD, PhD, RVT, Robert L. Kistner, MD, Bo Eklof, MD, PhD, Darcy Kessler, RVT, "Mechanism of venous valve closure and role of the valve in circulation: A new concept," *Journal of Vascular Surgery*, vol. 38, No. 5, 955-961, (2003).

Jonathan A. Phillips, Charles A. Vacanti, Lawrence J. Bonassar, "Fibroblasts regulate contractile force independent of MMP activity in 3D-collagen," *Elsevier BBRC*, 312, 725-732 (2003).

R.A. Roeder, G.C. Lantz, DVM, L.A. Geddes, ME, PhD, FACC, FRSM, "Mechanical Remodeling of Small-Intestine Submucosa Small-Diameter Vascular Grafts—A Preliminary Report," *Biomedical Instrumentation & Technology*, 110-120 (2001).

G.E. Sandusky, Jr., S.F. Badylak, R.J. Morff, W.D. Johnson, G. Lantz, "Histologic Findings After In Vivo Placement of Small Intestine Submucosal Vascular Grafts and Saphenous Vein Grafts in the Carotid Artery in Dogs," *American Journal of Pathology*, vol. 140, No. 2, 317-324 (1992).

Staros, JV; "N-hydroxysulfosuccinimide active esters: bis(N-hydroxysulfosuccinimide) esters of two dicarboxylic acids are hydrophilic, membrane-impermeant, protein cross-linkers"; Biochemistry; Aug. 17, 1982;21(17):3950-5.

Ulrika Zagai, Karin Fredriksson, Stephen I. Rennard, Joachim Lundahl, C. Magnus Sköld, "Platelets stimulate fibroblast-mediated contraction of collagen gels," *Respiratory Research*, 4:13, (2003).

Janice M. Zaleskas, Bernd Kinner, Toby M. Freyman, Joannis V. Yannas, Lorna J. Gibson, Myron Spector, "Contractile forces generated by articular chondrocytes in collagen-glycosaminoglycan matrices," *Elsevier Biomaterials*, 25 1299-1308 (2004).

* cited by examiner

REMODELABLE PROSTHETIC VALVE

RELATED APPLICATIONS

This application claims the benefit under 35 U.S.C. §119 (e) of U.S. Provisional Application Ser. No. 60/988,981, filed Nov. 19, 2007. The co-pending U.S. patent application Ser. No. 11/616,159, entitled "Implantable Graft Material," filed Dec. 26, 2006 by Johnson et al., is incorporated herein by reference in its entirety.

TECHNICAL FIELD

The present invention relates to methods of treatment and medical devices for implantation in a body vessel. More particularly, preferred embodiments of the present invention relate to implantable medical devices including a remodelable material moveable from a first configuration to permit remodeling of the remodelable material to a second configuration functioning as a valve within the body vessel.

BACKGROUND

Many vessels in animals transport fluids from one body location to another. Frequently, fluid flows in a substantially unidirectional manner along the length of the vessel. Native valves within the heart and veins function to regulate blood flow within the body. Heart valves positioned within the heart direct the flow of blood to and from other organs and pump oxygenated blood to the rest of the body. Venous valves are typically bicuspid valves positioned at varying intervals within veins to permit substantially unidirectional blood to flow toward the heart. Body vessels such as veins transport blood to the heart and arteries carry blood away from the heart. Occasionally, congenital defects or injury to valves within a body vessel can result in an undesirable amount of retrograde fluid flow across a valve therein, and compromise the unidirectional flow of fluid across the valve.

Various implantable medical devices are advantageously inserted within various portions of the body. Minimally invasive techniques and instruments for placement of intraluminal medical devices have been developed to treat and repair undesirable conditions within body vessels, including treatment of conditions that affect blood flow such as venous valve insufficiency. Various percutaneous methods of implanting medical devices within the body using intraluminal transcatheter delivery systems can be used to treat a variety of conditions. One or more intraluminal medical devices can be introduced to a point of treatment within a body vessel using a delivery catheter device passed through the vasculature communicating between a remote introductory location and the implantation site, and released from the delivery catheter device at the point of treatment within the body vessel. Intraluminal medical devices can be deployed in a body vessel at a point of treatment and the delivery device subsequently withdrawn from the vessel, while the medical device retained within the vessel to provide sustained improvement in valve function or to increase vessel patency. For example, an implanted medical device can improve the function of native valves by blocking or reducing retrograde fluid flow. Alternatively, a prosthetic valve can be implanted to replace the function of damaged or absent native valves within the body.

One challenge for development of a prosthetic valve with the venous system is mitigating thrombus formation that can occlude the vessel and/or lead to loss of functionality of the valve structures that regulate blood flow. In contrast to the arterial system, the lower flow rates in some body vessels such as the deep veins of the legs and feet can lead to stagnation of blood in the pockets about the bases of the leaflets or valve structure due to the inability of the blood to be flushed and refreshed thereabout. The pockets can fill with thrombus that compromises the ability the leaflets or valve structure to open and close in response to antegrade and retrograde flow (i.e., pressure differentials across the valve). For example, fibrinogen absorbed on to the surface of an implanted prosthetic valve can form a layer that triggers the biochemical pathway leading fibrin deposition, platelet aggregation, and thrombus formation.

Remodelable materials, such as extracellular matrices (ECM), can be used to provide a thrombo-resistant surface in an implantable prosthetic valve. Prosthetic valves desirably include valve leaflets formed from a remodelable material such that, upon implantation, the remodelable material can be used to form a permanently non-thrombogenic leaflet surface. Small intestinal submucosa (SIS) is a commercially available ECM material (Cook Biotech Inc., West Lafayette, Ind.) derived from a porcine source and processed to retain remodelability.

When implanted in some vessels such as veins, however, remodelable material is often subjected to intermittent fluid flow with intervals of blood stagnation. Changes in the flow rate, flow direction or fluid pressure of intraluminal fluid across an implanted remodelable material have the potential to disrupt or slow the remodeling process. The intraluminal fluid flow can be characterized by parameters such as pressure, direction, composition and flow rate across the interface. Intraluminal fluid flow in a vascular environment is subject to regular modulations in pressure and fluid flow due to respiratory and calf muscle function. The remodeling process itself may be linked to the flow of fluid across the remodelable surface. Recent investigations have shown that SIS-based remodeling of implanted medical devices can occur by recruitment of cells directly from intraluminal circulation. See Brountzos, et al, "Remodeling of suspended small intestinal submucosa venous valve: an experimental study in sheep to assess the host cells' origin," *J. Vasc. Interv. Radiol.*, 14(3), 349-356 (March 2003).

While the ability of valve leaflets made of ECM materials to remodel has been demonstrated clinically, the surface of the newly-implanted ECM materials such as SIS can be vulnerable to thrombus formation, particularly in sinus regions near valves. Because remodeling is a process that can take days, weeks or longer, depending on the environment, thrombogenicity has remained a clinical issue to be addressed when using remodelable biomaterials. In particular, implantable valves having valve leaflets comprising a remodelable material may thicken or undergo thrombotic deposition during the remodeling period within the body vessel. This may be the result of progressive fibrin deposition due to hemodynamics of blood flow contacting a portion of the valve leaflet near the wall of the body vessel. For example, blood may stagnate in the sinus defined by a valve leaflet and an adjacent portion of the body vessel wall. As a result, during remodeling of the valve leaflet after implantation, the thickness of the valve leaflet may increase on the upstream side of the valve leaflet upon endothelialization and the downstream side of the leaflet may sustain fibrin deposition and progressive thrombogenic deposition without significant endothelialization. The resulting thickening of the valve leaflet and/or fibrotic deposition thereon may reduce or compromise valve function of the remodeled valve leaflet within a period of about 3-6 weeks.

What is needed are prosthetic valves that provide for remodeling of at least a portion of the valve while reducing exposure of the remodelable material to conditions that may undesirably permit or promote the deposition of thrombogenic material on the remodelable material or thickening of the valve leaflet during remodeling. A prosthetic valve configured to permit contact of a remodelable valve leaflet with blood or tissue that promotes remodeling for a time period effective for remodeling prior to configuring the valve leaflet as an operable configuration to regulate fluid flow would be particularly desirable.

SUMMARY

Prosthetic medical devices may be configured to maintain a remodelable material within a body vessel in at least two different configurations: a first configuration suitable to contact the remodelable material with a body fluid for a first time period and a second configuration adapted to regulate the direction of body fluid contacting the remodelable material. Preferably, the body fluid flow is blood flow across the remodelable material within a body vessel, such as a venous valve or a heart valve. In the first configuration, the remodelable material is preferably in contact with the fluid flow while being positioned in a manner permitting blood flow to remain in moving contact with the remodelable material. For example, the remodelable material in the first configuration may be oriented as a substantially flat sheet substantially parallel to the longitudinal axis of a body vessel, preferably without contacting the wall of the body vessel, to permit blood flow to pass around and contact the remodelable material. The medical device may be configured and adapted to maintain the remodelable material in the first configuration for a period of time effective to remodel (i.e., a remodeling-effective period of time) at least a portion of the remodelable material by contact with the body fluid. For example, the time period may be several days, weeks or months (e.g., 14-90 days). In moving from the first configuration to a second configuration, the remodelable material may change shape, configuration or orientation within the body vessel to extend across at least a portion of the body vessel and provide a valve function to regulate fluid flow within the body vessel in a substantially unidirectional manner while in the second configuration. The remodelable material in the second configuration may be configured as one or more valve leaflets forming a heart valve or venous valve.

In a first embodiment, an implantable prosthetic valve assembly may include at least one valve leaflet comprising a remodelable material attached to a support frame and a releasable holding member configured to restrain the valve leaflet in the first configuration for a desired period of time. The period of time is preferably effective to provide a desired degree of remodeling within the valve leaflet by contact with a body tissue or fluid, such as blood. The support frame may have any suitable structure. For example, a support frame may define a lumen extending from a proximal end to a distal end along a longitudinal axis and be configured for implantation within a body vessel. The valve leaflet may be attached to the support frame and oriented in a first configuration within the lumen permitting a bidirectional fluid flow through the lumen in a first direction along the longitudinal axis and a second direction opposite the first direction Preferably, the valve leaflet is moveable from the first configuration to a second configuration permitting fluid flow through the lumen in the first direction while substantially limiting fluid flow through the lumen in the direction opposite the first direction. The release member may simultaneously prevent the valve leaflet from moving to the second configuration. The valve leaflet is preferably moveable to the second configuration within the lumen upon release of the leaflet holding member The releasable holding member may include a bioabsorbable polymer selected to dissipate within a body vessel within the period of time for a desired extent of remodeling to occur within the valve leaflet in contact with a body fluid, such as 14 to 90 days.

The valve leaflet may be maintained in the first configuration inside a body vessel or other body cavity that is the same or different from the location of the valve leaflet in the second configuration. In one aspect, the valve leaflet may be implanted within a body cavity in a first configuration for a period of time to permit a desired degree of remodeling of the remodelable material therein, subsequently explanted and placed at a second point of treatment within the body of the same or a different subject. The valve leaflet may be moved from the first configuration to a second configuration prior to or after placement at the second point of treatment. The second configuration is preferably adapted to provide a valving function within the body vessel. More preferably, the prosthetic valve assembly is placed at a single point of treatment within a blood vessel in the first configuration. Upon release of the valve leaflet holding member, the valve leaflet may change from the first configuration that does not regulate fluid to the second configuration providing a substantially unidirectional fluid regulating function within the body vessel. For example, a valve leaflet in the second configuration may extend from a base portion contacting a portion of the support frame to a free edge portion distal to the base portion. The free edge may be flexibly moveable within the lumen to define at least a portion of a valve orifice moveable therein to permit the fluid flow through the lumen in the first direction while substantially limiting fluid flow through the lumen in the direction opposite the first direction. The valve leaflets in the first configuration may be oriented in a manner permitting fluid flow across the surface of the remodelable material without providing stagnation of fluid contacting the remodelable material. The prosthetic valve assembly is preferably adapted to permit one or more valve leaflets to change orientation from the first configuration to a second configuration upon contact with a body fluid or tissue for a desired period of time, preferably a remodeling-effective period of time. For example, release of the leaflet holding member may result in the change in orientation of one or more valve leaflets from the first configuration to the second configuration. In the second configuration, the valve leaflets are preferably oriented to regulate fluid flow and may contact a portion of a body vessel wall. In the second configuration, static fluid may contact portions of the valve leaflets during periods of retrograde fluid flow, as fluid collects between the closed valve leaflets and the wall of the body vessel.

Preferably, the support frame comprises a self-expanding material, such as a nickel titanium alloy, spring metals, stainless steel and shape memory polymers, configured to urge the valve leaflet from the first configuration toward the second configuration in the absence of the releasable leaflet holding member. A valve leaflet in the first configuration may be a sheet substantially parallel to the longitudinal axis of the body vessel or support frame. For instance, the valve leaflet in the first configuration may be configured as a substantially flat sheet contained within the lumen defined by the support frame.

The valve leaflet(s) can provide a valve function to the implantable medical device when the valve leaflet(s) are in the second configuration, with one or more edges of the leaflet(s) preferably defining at least a portion of the valve orifice of a prosthetic valve. A valve leaflet can provide a valve function by moving between the first and second configurations relative to one another. When the valve orifice is in an open position, the leaflet substantially blocks the lumen of the vessel; in the closed position, the lumen is substantially blocked. Thus, the leaflet(s) permits fluid to flow through the vessel in a first direction when in the first (open) configuration, and substantially prevents fluid flow through the vessel in a second, opposite direction when in the second (closed) configuration. The valve leaflet(s) can be formed of a remodelable material, such as small intestine submucosa (SIS) or other extracellular matrix (ECM) material. The valve leaflet(s) may also be formed from a non-remodelable material having a remodelable material or remodeling encouraging material attached to the non-remodelable material. The valve leaflet(s) may be attached to a support frame in any suitable manner. The one or more leaflets are optionally attached to a support structure that is moveable from a radially compressed to a radially expanded configuration. The support frame can comprise any suitable support frame, including self-expandable, mechanically expandable, wire, tube, metal, polymeric, composite and other types of support frames.

In a second embodiment, methods of treatment may include the steps of implanting the medical devices according to the first embodiment are provided. The medical devices are preferably adapted for transcatheter percutaneous delivery in a body vessel, and can radially expand at a point of treatment. The medical devices can have any suitable configuration, but preferably include one or more valve leaflets attached to the support frame in the first configuration.

In a third embodiment, methods of manufacturing the implantable medical devices of the first embodiment are provided. The methods may include the step of attaching a valve leaflet including a remodelable material to a support frame extending along a longitudinal axis and being configured for implantation within a body vessel. The valve leaflet may be attached to the support frame oriented in a first configuration permitting a bidirectional longitudinal fluid flow past the leaflet along the longitudinal axis of the support frame, the medical device and/or a body vessel in both a first direction and a second direction opposite the first direction. In addition, the valve leaflet is preferably moveable from the first configuration to a second configuration permitting fluid flow along the longitudinal axis of the medical device in the first direction while substantially limiting fluid flow through the lumen in the direction opposite the first direction. The methods may also include the step of attaching to the support frame a releasable holding member for restraining the valve leaflet in the first configuration. Preferably, the releasable holding member simultaneously prevents the valve leaflet from moving to the second configuration. The valve leaflet is preferably moveable to the second configuration within the lumen upon release of the holding member.

The invention includes other embodiments within the scope of the claims, and variations of all embodiments, and is limited only by the claims made by the Applicants. Additional understanding of the invention can be obtained by referencing the detailed description of embodiments of the invention, below, and the appended drawings.

DETAILED DESCRIPTION

Figure 1A:
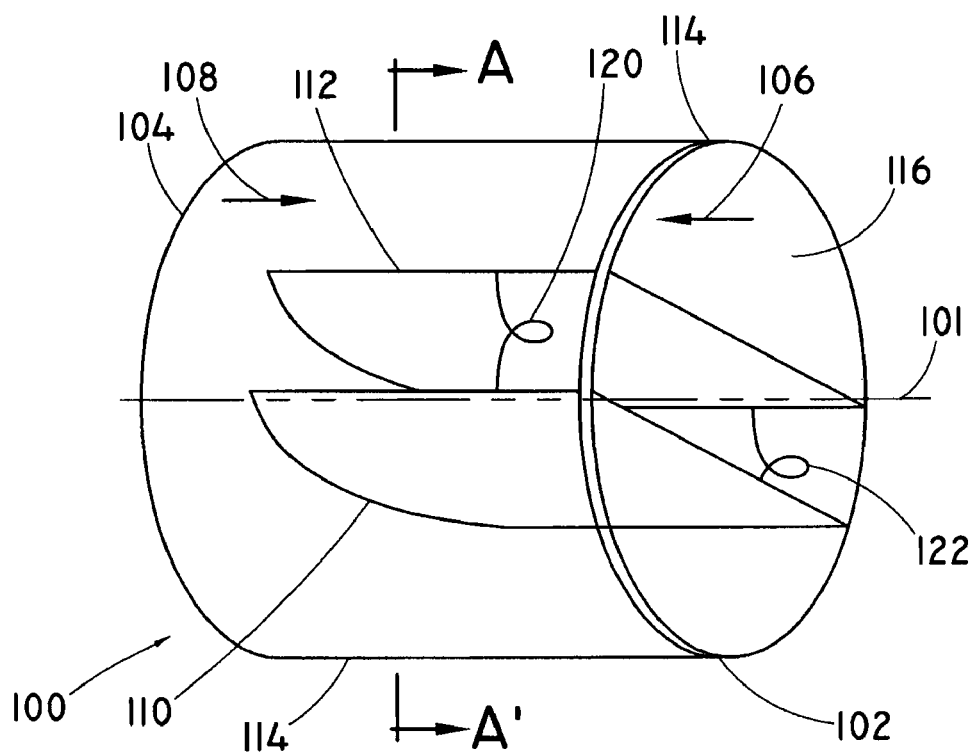
FIG. 1A is a perspective view of a first prosthetic valve assembly having two leaflets in a first configuration.

The following detailed description and appended drawings describe and illustrate various exemplary embodiments of the invention. The description and drawings serve to enable one skilled in the art to make and use the invention.

Definitions

As used herein, the term "implantable" refers to an ability of a medical device to be positioned at a location within a body, such as within a body vessel. Furthermore, the terms "implantation" and "implanted" refer to the positioning of a medical device at a location within a body, such as within a body vessel.

The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause an undesirably adverse, long-lived or escalating biological reaction or response, and is distinguished from a mild, transient inflammation which typically accompanies surgery or implantation of foreign objects into a living organism.

A large number of different types of materials are known in the art which may be inserted within the body and later dissipate. The term "bioabsorbable" is used herein to refer to materials selected to dissipate upon implantation within a body, independent of which mechanisms by which dissipation can occur, such as dissolution, degradation, absorption and excretion. The terms "bioabsorbable," "absorbable," or "biodegradable" are used synonymously herein, unless otherwise specified, to refer to the ability of the material or its degradation products to be removed by biological events, such as by fluid transport away from the site of implantation or by cellular activity (e.g., phagocytosis). Only the term "bioabsorbable" will be used in the following description to encompass absorbable, absorbable, bioabsorbable, and biodegradable, without implying the exclusion of the other classes of materials. "Non-bioabsorbable" material refers to a material, such as a polymer or copolymer, which remains in the body without substantial bioabsorption.

The terms "remodelable" or "bioremodelable" as used herein refer to the ability of a material to allow or induce host tissue growth, proliferation or regeneration following implantation of the tissue in vivo. Remodeling can occur in various microenvironments within a body, including without limitation soft tissue, a sphincter muscle region, body wall, tendon, ligament, bone and cardiovascular tissues. Upon implantation of a remodelable material, cellular infiltration and neovascularization are typically observed over a period of about 5 days to about 6 months or longer, as the remodelable material acts as a matrix for the ingrowth of adjacent tissue with site-specific structural and functional properties. The remodeling phenomenon which occurs in mammals following implantation of submucosal tissue includes rapid neovascularization and early mononuclear cell accumulation. Mesenchymal and epithelial cell proliferation and differentiation are typically observed by one week after in vivo implantation and extensive deposition of new extracellular matrix occurs almost immediately. The term "non-remodelable" refers to a material that is not a remodelable material that is not selected or configured to promote or induce tissue growth upon contacting living tissue. A non-remodelable material preferably does not contain biological molecules (such as growth factors) that promote tissue ingrowth, angiogenesis, and other growth processes within the material. Non-remodelable materials may include biostable or bioabsorbable polymers, as well as forms of collagen or other biomolecules configured or treated to slow tissue ingrowth. For example, a cross-linked extracellular matrix material configured and treated to substantially retard or prevent tissue ingrowth can also be used as a non-remodelable material. Non-remodelable materials may also be provided with materials such as ligands or ECM attached to the nonremodelable material to promote remodeling.

As used herein, the term "body vessel" means any body passage lumen that conducts fluid, including but not limited to blood vessels, esophageal, intestinal, billiary, urethral and uretheral passages.

The term "alloy" refers to a substance composed of two or more metals or of a metal and a nonmetal intimately united, for example by chemical or physical interaction. Alloys can be formed by various methods, including being fused together and dissolving in each other when molten, although molten processing is not a requirement for a material to be within the scope of the term "alloy." As understood in the art, an alloy will typically have physical or chemical properties that are different from its components.

The term "mixture" refers to a combination of two or more substances in which each substance retains its own chemical identity and properties.

The medical devices of the embodiments described herein may be oriented in any suitable absolute orientation with respect to a body vessel. The recitation of a "first" direction is provided as an example. Any suitable orientation or direction may correspond to a "first" direction. The medical devices of the embodiments described herein may be oriented in any suitable absolute orientation with respect to a body vessel. For example, the first direction can be a radial direction in some embodiments.

The terms "frame" and "support frame" are used interchangeably herein to refer to a structure that can be implanted, or adapted for implantation, within the lumen of a body vessel. As used herein, a "support frame" is any structure that is attached to the remodelable material, for example to hold a remodelable leaflet in place within a body vessel, including an interior portion of a blood vessel, lymph vessel, ureter, bile duct or portion of the alimentary canal. A "valve support frame," as used herein, refers to a support frame that forms a portion of a valve means for modifying fluid flow within a body vessel. The valve support frame can have any suitable configuration, but is preferably a radially expandable structure comprising a plurality of struts and bends and enclosing an interior lumen. Preferably, one or more valve leaflets can be attached to the valve support frame.

As used herein, "retrograde flow across a valve" refers to fluid flow in a direction other than the primary (antegrade) direction of fluid flow when the valve is open and functioning correctly. Retrograde flow typically proceeds in a direction opposite the direction of fluid through the open valve. Retrograde flow can occur when the valve is in the open or closed position, through a valve orifice or through other apertures in a valve surface. For example, for a valve in a vein, retrograde flow proceeds in the direction away from the heart. For a heart valve, retrograde flow can occur when the valve is in a closed position and can lead to various medical complications.

As used herein, "valve orifice" refers to an opening in a valve moveable between an open position permitting fluid flow through the valve orifice, and a closed position that substantially prevents fluid flow through the valve orifice. The valve orifice can be defined by the opposably positioned edges of one or more valve leaflets. The valve orifice can be defined by any suitable number of valve leaflets. Preferably, the valve orifice can be defined by two or three valve leaflets to form a bicuspid or tricuspid valve, respectively.

As used herein, "retrograde valve aperture" refers to an opening in the surface of the valve other than the valve orifice that permits retrograde fluid flow therethrough. Apertures can include holes placed in previously implanted prosthetic valve leaflets to promote remodeling of an extracellular matrix leaflet material.

Implantable Medical Devices

In a first embodiment, prosthetic medical devices are provided. Preferably, the medical devices are adapted to maintain a remodelable material in at least two configurations. The material itself may be remodelable (such as an extracellular matrix material) or may be formed from a non-remodelable material (such as a polymeric material) provided with a material such as a ligand or extracellular matrix material, attached to the nonremodelable material to promote remodeling. The medical device may be configured to reorient or reposition the remodelable material from a first configuration permitting remodeling of the remodelable material within a body vessel, to a second configuration permitting the remodelable material to function as a valve leaflet operable to regulate fluid flow through the body vessel. Preferably, the medical device is configured to move the remodelable material from the first configuration to the second configuration without intervention after a period of time suitable for remodeling of at least a portion of the remodelable material. The medical device may include a releasable holding member for maintaining the remodelable material in the first configuration and may be configured to move the remodelable material to the second configuration upon release of the holding member. The medical devices may be adapted for implantation within a blood vessel and permit contact between a remodelable material attached to a support frame and blood within the body vessel. In the first configuration, the remodelable material may be a sheet of extracellular matrix material or a sheet of nonremodelable material having a remodelable material attached thereto maintained within a body vessel in contact with dynamic body fluid flow, substantially without contact between the remodelable material and static body fluid. Also preferably, the prosthetic medical device is configured to initially maintain the remodelable material without contacting the body vessel upon implantation.

Figure 1B:
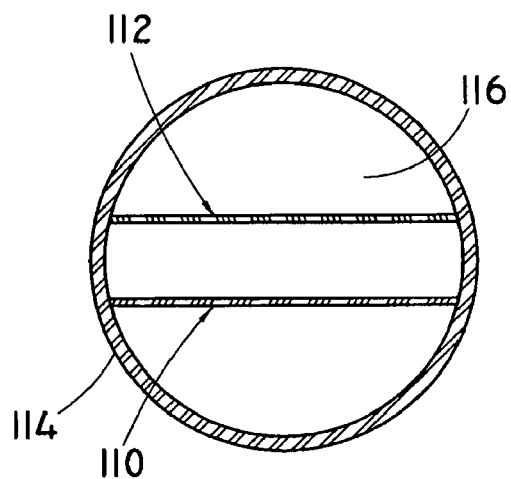
FIG. 1B is cross-sectional view of the native valve along line A-A' shown in FIG. 1A.

FIG. 1A is a perspective view of a prosthetic valve assembly having two leaflets in a first configuration. A prosthetic valve assembly 100 includes a support frame 114, a first valve leaflet 110 and a second valve leaflet 112. The support frame 114 defines a lumen 116 extending from a proximal end 102 to a distal end 104 along a longitudinal axis 101. The support frame 114 can have any suitable configuration configured for implantation within a body vessel. For example, the support frame 114 may be formed from a biocompatible metal or alloy configured as a plurality of interconnected struts and bends. A series of sinusoidal hoop members may be longitudinally spaced apart, axially aligned along the longitudinal axis 101 and interconnected by a plurality of connecting members to form the support frame 114, shown as a cylinder in FIG. 1A. The prosthetic valve assembly 100 is shown in a first configuration in FIG. 1A, having the two valve leaflets 110, 112 oriented substantially parallel to one another and symmetrically stacked on either side of the longitudinal axis 101 within the lumen 116. FIG. 1B is cross-sectional view of the prosthetic valve along line A-A' shown in FIG. 1A, showing the first valve leaflet 110, the second valve leaflet 112, the lumen 116 and the support frame 114. The first valve leaflet 110 and the second valve leaflet 112 in the first configuration may be oriented to permit fluid to flow through the lumen in contact with the both sides of the valve leaflets 110, 112 without reducing the rate of fluid flow in the first direction 106 relative to fluid flow in the second direction 108, thereby permitting bidirectional flow through the lumen 116.

Preferably, each valve leaflet includes a remodelable material and is maintained in contact with blood while the prosthetic valve assembly 100 is in the first configuration. A remodelable material can undergo biological processes such as angiogenesis when placed in communication with a living tissue, such that the remodelable material is biologically transformed into material that is substantially similar to said living tissue in cellular composition. Unless otherwise specified herein, a "remodelable material" can include a single layer material, or multiple layers of one or more materials that together undergo remodeling when placed in communication with living tissue. The remodelable material can provide an acellular scaffold or matrix that can be populated by cells. One example of a remodeling process is the migration of cells into the remodelable material. Migration of cells into the remodelable material can occur in various ways, including contact with blood. Preferably, a remodelable valve leaflet is placed within the lumen 116 of the support frame 114 in the first configuration shown in FIGS. 1A and 1B without contacting the wall of a body vessel upon implantation. During blood contact with the remodelable material, recruitment of cells from tissue at a remote location may occur when blood contacts the remodelable material, permitting in situ remodeling of the valve leaflet upon implantation. See, e.g., Brountzos, et al, "Remodeling of suspended small intestinal submucosa venous valve: an experimental study in sheep to assess the host cells' origin," *J. Vasc. Interv. Radiol.*, 14(3), 349-356 (March 2003), this disclosure of which pertaining to the formation of implantable prosthetic valves and the implantation of the valves within a body vessel is incorporated herein by reference. The migration of cells into the remodelable material can impart improved function to the remodelable material and reduce incidence of thrombosis. In some embodiments, the remodelable material itself can be absorbed by biological processes. Non-limiting examples of remodelable materials, their preparation and use are also discussed herein. Preferably, a remodelable valve leaflet material remains in the first configuration within a body vessel while undergoing a desired degree of remodeling upon contact for about 90 days or less with living tissue of the type present at an intended site of implantation, such as the interior of a body vessel.

Figure 2A:
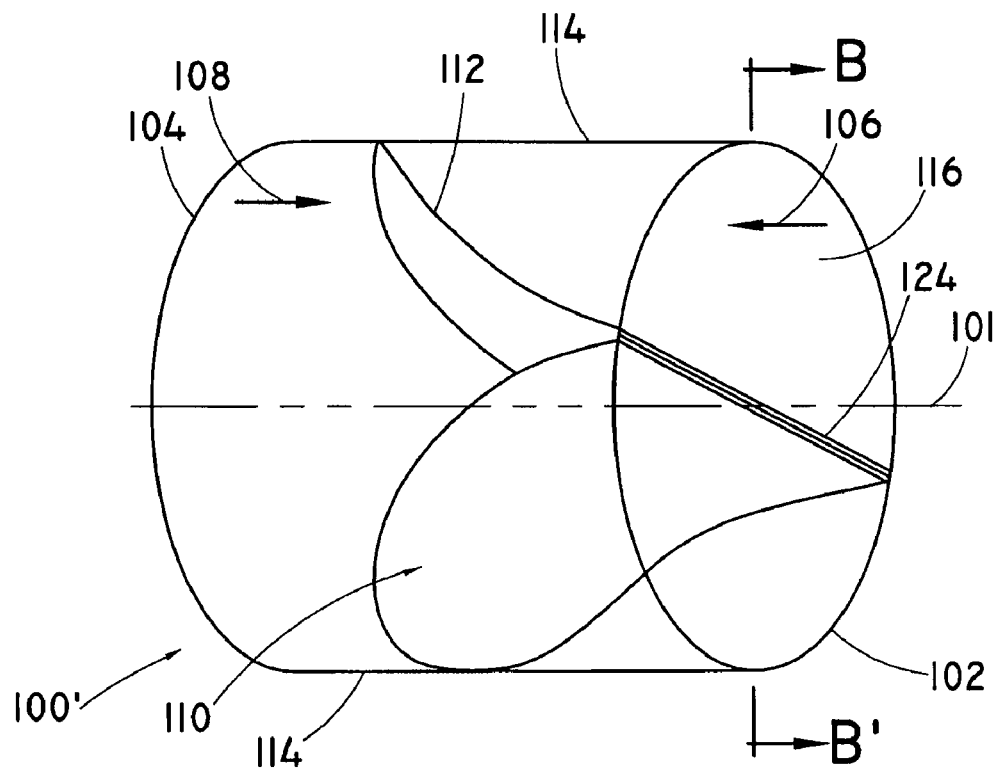
FIG. 2A is a perspective view of the first prosthetic valve assembly of FIG. 1A having two leaflets in a second configuration.
Figure 2B:
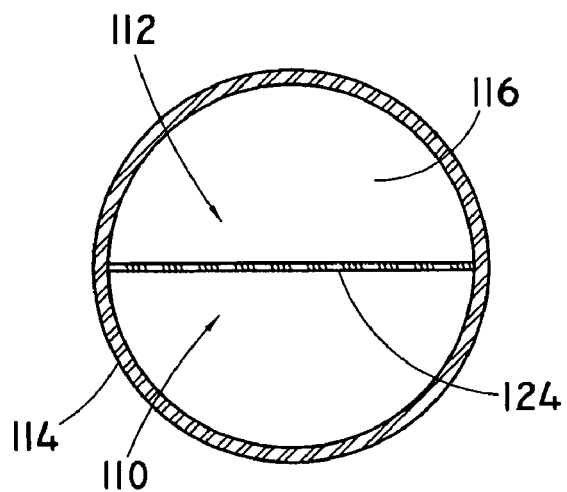
FIG. 2B is cross-sectional view of the first prosthetic valve assembly along line B-B' shown in FIG. 2A.

The valve leaflets 110, 112 of the prosthetic valve assembly 100 are moveable to a second configuration shown in FIGS. 2A and 2B. FIG. 2B is an end view of the prosthetic valve assembly 100 shown in FIG. 2A along line B-B' showing the prosthetic valve assembly 100 in a second, closed configuration. The prosthetic valve assembly 100' (in the second configuration) may have one or more valve leaflets 110, 112 shaped and oriented in any suitable manner. However, while the valve leaflets 110, 112 in the first prosthetic valve assembly configuration are preferably shaped and oriented to permit fluid to flow through the lumen 116 in both a first direction 106 and a second direction 108 opposite the first direction 106, the valve leaflets 110, 112 in the second configuration are preferably shaped and oriented to permit fluid flow in only the second direction 108 (while blocking or reducing the rate of fluid flow in the first direction 106). The first direction 106 and the second direction 108 may be oriented along the longitudinal axis 101. Compared to the first configuration shown in FIGS. 1A and 1B, the valve leaflets 110, 112 in the second configuration 100' are re-oriented relative to one another and/or relative to the support frame 114 so as to provide a valve function. Preferably, the second configuration 100' is adapted to permit fluid flow through the lumen 116 in the first direction 106 while substantially limiting fluid flow through the lumen in the second direction 108 opposite the first direction 106. For example, the proximal edges of the first valve leaflet 110 and the second valve leaflet 112 near the proximal end 102 of the support frame 114 are tilted toward one another in the second configuration to form a valve orifice 124. The distal edges of the first valve leaflet 110 and the second valve leaflet 112 near the distal end 104 of the frame 114 are tilted away from each other in the second configuration, and away from the longitudinal axis 101, to sealably engage a portion of the support frame 114. Each valve leaflet 110, 112 may be flexible enough to move toward or away from the longitudinal axis 101 in response to fluid flow contacting each valve leaflet 110, 112 within the lumen 116. Fluid flow in the first direction 106 contacts the proximal side of the valve leaflets 110, 112 and urges the proximal edge of the valve leaflets 110, 112 toward the longitudinal axis 101, closing the valve orifice 124 as shown in FIGS. 2A and 2B, and preventing fluid flow in the first direction 106. Conversely, fluid flow in the second direction 108 contacts the distal side of the valve leaflets 110, 112 and urges the proximal edge of the valve leaflets 110, 112 away from the longitudinal axis, opening the valve orifice 124 and permitting fluid flow in the second direction 108.

Preferably, a prosthetic valve assembly is configured to move a remodelable material from a first configuration to a second configuration within a body vessel. The prosthetic valve assembly may be configured to resist fluid flow through a lumen defined by a support frame in a first longitudinal direction relative to a second longitudinal direction opposite the first direction to a greater degree when the remodelable material is in the second configuration than when the remodelable material is in the first configuration. Preferably, the resistance to fluid flow in at least one direction is at least 20% (preferably about 20-100%) greater in the second configuration compared to the first configuration. For example, the prosthetic valve assembly 100 has two valve leaflets 110, 112 oriented substantially parallel to one another in a first configuration shown in FIGS. 1A and 1B, and tilted toward one another at the proximal edges of the valve leaflets 110, 112 to form a valve orifice 124 in the second configuration shown in FIGS. 2A and 2B. The resistance to fluid flow through the lumen 116 of the prosthetic valve assembly 100 in the first direction 106 compared to the second direction 108 is greater when the valve leaflets 110, 112 are in the second configuration. In one aspect, the valve leaflets 110, 112 in the second configuration may be configured to prevent or substantially prevent fluid flow in the first direction 106.

The prosthetic valve assembly preferably includes a releasable holding member configured to restrain one or more leaflets having a remodelable material in the first configuration. The releasable holding member may be formed from materials that are bioabsorbable as described in more detail below. The releasable leaflet holding member may simultaneously prevent the valve leaflet(s) from moving to the second configuration. The releasable leaflet holding member may include a bioabsorbable means for restraining the valve leaflet and may comprise one or more bioabsorbable polymers or metals and is absorbable within a remodeling-effective period of time, such as about 14 days to 60 days after implantation within a blood vessel. The releasable holding member may also include mechanical devices that may be activated either at the delivery site or externally after the prosthetic valve has been implanted for a period of time with the valve leaflet(s) in the first configuration. For example, the mechanical device may include a latch connecting a portion of the frame to a portion of the leaflet that has a friable connection that may be released using an energy source to release the connection and allow the leaflets to move to the second configuration. Other structures such as temporary magnets or wires may also be used. For some mechanical devices, the releasable holding means may be released within the body lumen, for example by cutting a suture. Other types of mechanical holding mechanisms know to one skilled in the art may also be used. Examples provided below describe a bioabsorbable means for restraining the leaflet(s) in the first configuration. One skilled in the art will understand that mechanical releasable holding member may also be used in the devices described below.

By way of non-limiting example, the prosthetic valve assembly 100 includes one or more valve leaflet(s) 110, 112 moveable to the second configuration within the lumen upon release of the holding member. For example, the releasable leaflet holding member may be a first and a second bioabsorbable support frame portions 120, 122. The support frame 114 may include a radially self-expanding portion configured to return the valve leaflets 110, 112 in the second configuration absent the bioabsorbable support frame portions 120, 122. The valve leaflets 110, 112 may be attached to a portion of the support frame formed in the second configuration shown in FIGS. 2A and 2B. The valve leaflets 110, 112 may be moved to the first configuration shown in FIGS. 1A and 1B and the bioabsorbable support frame portions 120, 122 may be introduced to or attached to the support frame 114 to retain the valve leaflets 110, 112 in the first configuration.

The valve leaflet in a first configuration may be configured as a substantially flat sheet contained within the lumen defined by the support frame. The valve leaflet in the second configuration may extend from a base portion contacting a portion of the support frame to a free edge portion distal to the base portion. The free edge may be flexibly moveable within the lumen to define at least a portion of a valve orifice moveable therein to permit the fluid flow through the lumen in the first direction while substantially limiting fluid flow through the lumen in the direction opposite the first direction.

Figure 3A:
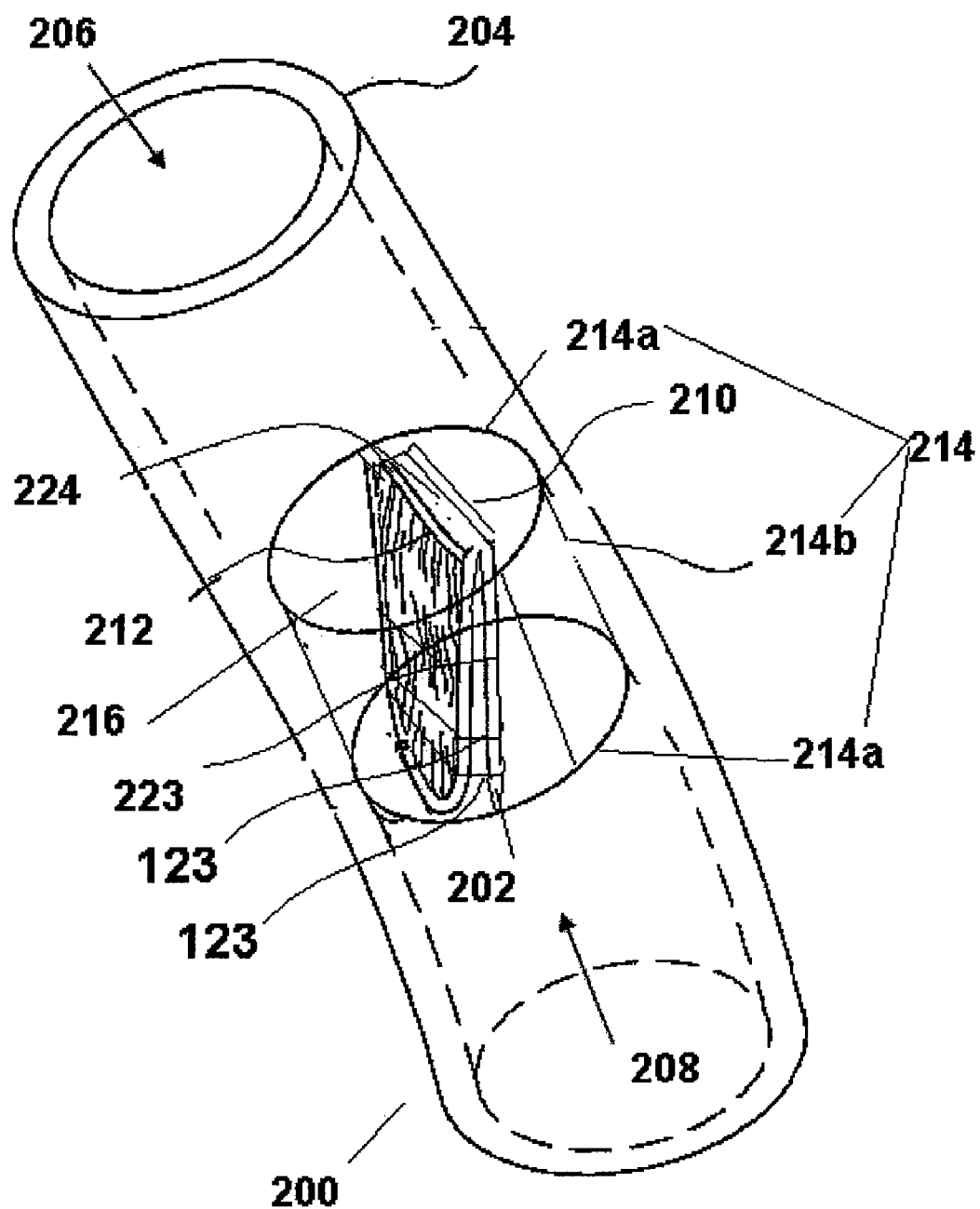
FIG. 3A is side view of a second prosthetic valve assembly positioned within a body vessel with a pair of valve leaflets in a planar configuration.
Figure 3B:
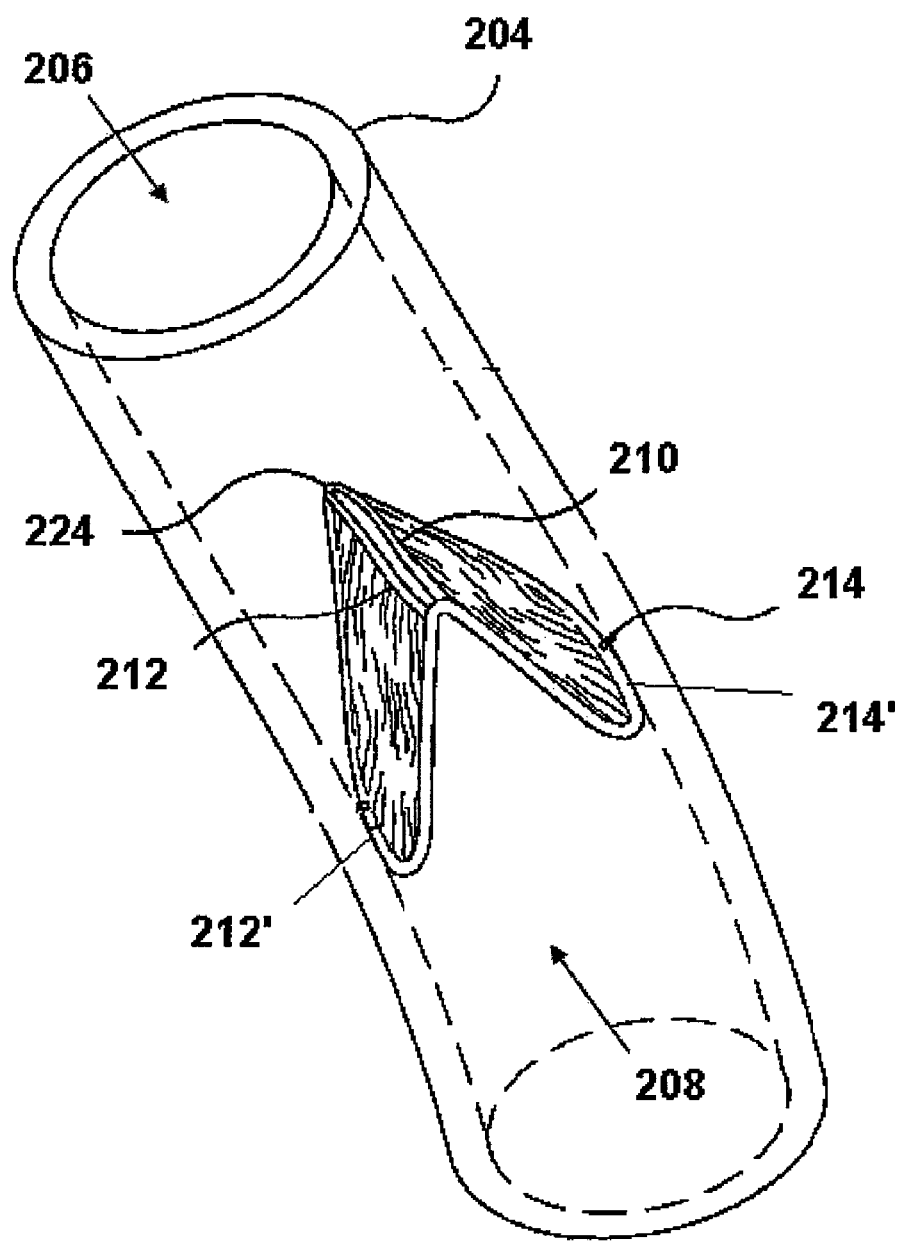
FIG. 3B is side view of the second prosthetic valve assembly shown in FIG. 3A positioned within the body vessel with the pair of valve leaflets in a second configuration and oriented to prevent retrograde fluid flow through the body vessel.
Figure 3C:
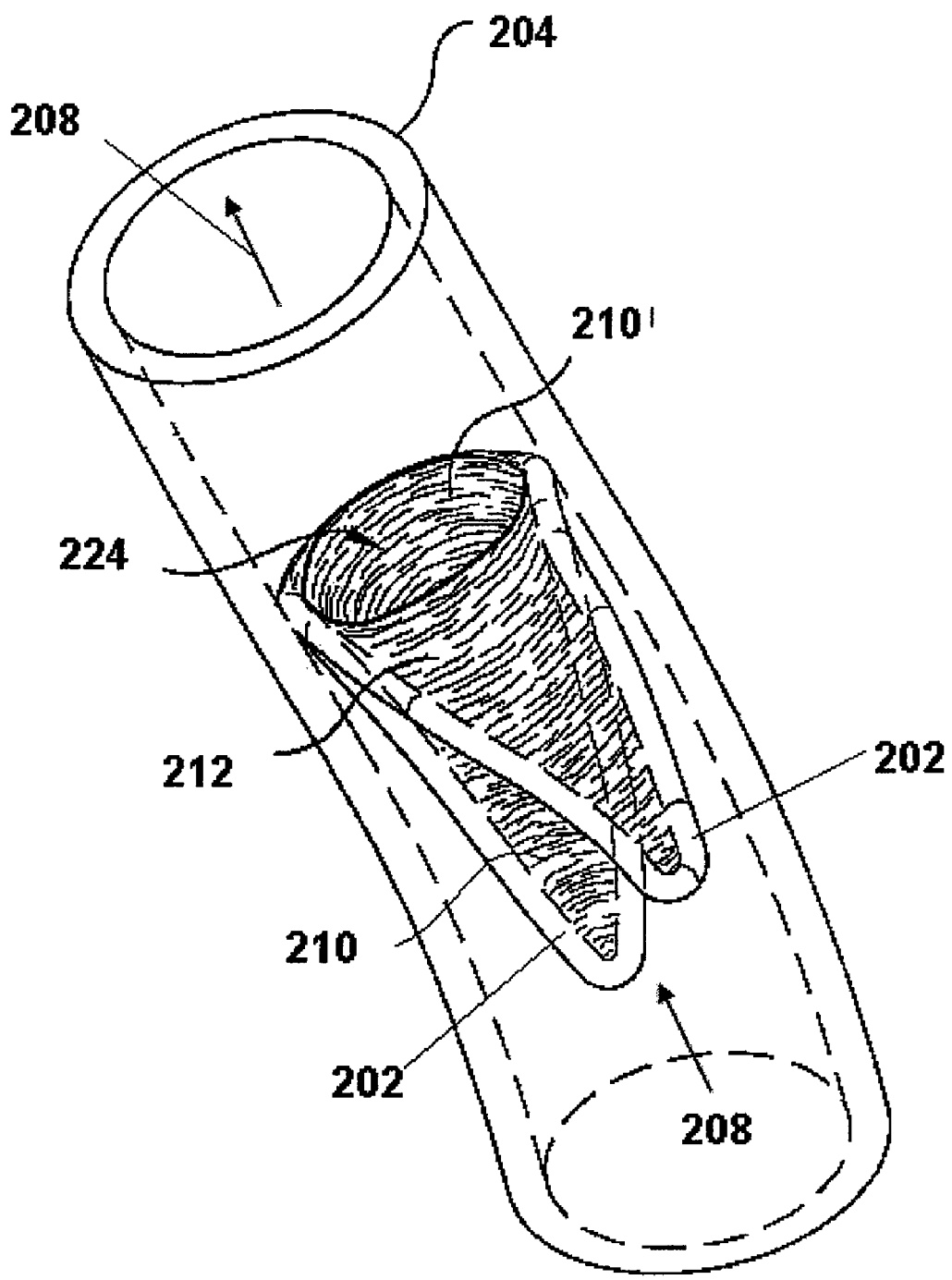
FIG. 3C is side view of the second prosthetic valve assembly shown in FIG. 3B positioned within the body vessel with the pair of valve leaflets in the tilted second configuration and oriented to permit antegrade fluid flow through the body vessel.

A second prosthetic valve assembly 200 may include a first support frame portion 202 that may be securely positioned within a second frame portion 214 before or after implantation in a body vessel 204. FIG. 3A is side view of a second prosthetic valve assembly 200 positioned within a body vessel 204 with a pair of valve leaflets 210, 212 in a planar configuration. FIG. 3B is side view of the second prosthetic valve assembly 200 shown in FIG. 3A positioned within the body vessel 204 with the pair of valve leaflets 210, 212 in a tilted configuration and oriented to prevent retrograde fluid flow through the body vessel 204. FIG. 3C is side view of the second prosthetic valve assembly 200 shown in FIG. 3B positioned within the body vessel 204 with the pair of valve leaflets 210, 212 in the tilted configuration and oriented to permit antegrade fluid flow through the body vessel 204. The first support frame portion 202 may be formed from a radially self-expanding biocompatible material configured as a plurality of alternating struts and bends to form a sinusoidal hoop member. The particular first frame portion 202 may be formed as a single member, for example, of shape memory metal (e.g., a superelastic nickel titanium alloy), biocompatible metal, or shape memory polymer, configured as an alternating array of a alternating series of four bends and four struts continuously connected in a pair of parallel connected "V" shapes. A first valve leaflet 210 and a second valve leaflet 212 are tensionably attached across opposing struts in the first frame portion 202, defining an orifice 223 at the proximal end of the first support frame portion 202. The first frame portion 202 is configured to resiliently expand to an expanded configuration shown in FIGS. 3B and 3C in the absence of a means for restraining the first frame portion 202 with the valve leaflets 210, 212 in the planar configuration of FIG. 3A. The second frame portion 214 may be a tubular structure adapted to receive the first frame portion 202 within a lumen defined between a pair of hoop members 214a and a plurality of longitudinal connecting members 214b extending therebetween. The hoop members 114a may have a ring-like structure as shown in FIG. 3A, or may be formed as one or more sinusoidal undulating ring structures. The second frame portion 214 need not be tubular as shown in the preferred embodiment of FIG. 3A, but may alternatively be formed in any manner suitable to securely receive the first frame portion 202 with a fixed orientation within the body vessel 204.

The second prosthetic valve assembly 200 may be assembled prior to, during or after implantation of the second frame portion 214. For example, a "cartridge" comprising the valve leaflets 210, 212 attached to the first frame portion 202 may be seated within the second frame portion 214 inside the body vessel. The first frame portion 202 may be positioned within the second frame portion 214 with the longitudinal axes of the first frame portion 202 and the second frame portion 214 aligned with the longitudinal axis of the second prosthetic valve assembly 200. Upon implantation within the body vessel 204, the longitudinal axis of the prosthetic valve assembly 200 may be aligned parallel to the longitudinal axis of the body vessel 204.

The prosthetic valve assembly 210 may be assembled within the body vessel 204, or prior to implantation therein. In the first instance, a second frame portion 214 may be implanted at a point of treatment within a body vessel. The cartridge comprising the first frame portion 202 and valve leaflets 210, 212 may be secured to the second frame portion 214 inside the body vessel at the time the second frame portion 214 is implanted, or in a subsequent procedure performed after implanting the second frame portion 214. Optionally, the cartridge comprising a first valve leaflet 210 formed from a remodelable material may be contacted with blood, tissue or other biological material prior to implantation of the cartridge within the second frame portion 214. One or more of the valve leaflets 210, 212 comprising remodelable material may be contacted with a biological material to induce remodeling in the valve leaflet attached to the cartridge prior to placement of the cartridge within the second frame portion 214 within a body vessel 204. For example, published US patent application US2007/0154515 A1, filed Dec. 26, 2006 by Johnson et al., describes a method of contacting a remodelable material with biological material (e.g., blood, tissue, and the like) to induce remodeling in the material prior to placing the material at a preferred treatment site within a body vessel.

The cartridge comprising the first frame portion 202 preferably maintains the valve leaflets 210, 212 in a parallel planar configuration shown in FIG. 3A. The cartridge may include a self-expandable first support frame portion 202 configured for implantation within a body vessel and having a longitudinal axis. The first valve leaflet 210 and the second valve leaflet 212 are shown in FIG. 3A in the parallel configuration permitting a bidirectional fluid flow along the longitudinal axis of the first support frame portion 202 in both a first longitudinal direction and a second longitudinal direction opposite the first direction. The first valve leaflet 210 and the second valve leaflet 212 may each include a remodelable material and extend from a leaflet base to a leaflet free edge distal to the leaflet base. The free edges are oriented to form a flexible orifice 224 in both the planar and tilted configurations. The first valve leaflet 210 and the second valve leaflet 212 may each be separately attached to the first support frame portion 202 in a substantially planar configuration oriented substantially parallel to each other along the longitudinal axis of the body vessel 204 and/or the first support frame portion 202. The first support frame portion 202 is configured to permit the first valve leaflet 210 and the second valve leaflet 212 to move from the planar configuration to a tilted configuration shown in FIGS. 3A and 3B. The tilted configuration provides the free edge of the first valve leaflet 210 in contact with the free edge of the second valve leaflet 212 to form at least a portion of a valve orifice 224. The base of the first valve leaflet 210 and the base of the second valve leaflet 212 are each positioned a greater distance from the longitudinal axis of the first support frame portion 202 in the tilted configuration than in the planar configuration. The prosthetic valve assembly 200 including the valve leaflets 210, 212 in the tilted configuration permits fluid flow along the longitudinal axis of the prosthetic valve assembly 200 in the first longitudinal direction while substantially limiting fluid flow in the second longitudinal direction opposite the first direction.

The cartridge with the valve leaflets 210, 212 attached to the first support frame portion 202 may be configured to resiliently expand to the tilted configuration absent a means for restraining the valve leaflets in the planar configuration. Preferably, the cartridge includes a bioabsorbable means for restraining the valve leaflets 210, 212 in the planar configuration, and/or simultaneously preventing each valve leaflet from moving to the tilted configuration. The valve leaflets 210, 212 are preferably moveable to the tilted configuration upon release of the leaflet holding member. For example, the bioabsorbable means for restraining the valve leaflets 210, 212 in the planar configuration may be one or more bioabsorbable threads 223 wrapped around the first support frame portion 202 with the leaflets 210, 212 in the planar configuration. Upon bioabsorption of the bioabsorbable threads 223 in situ, the first support frame portion 202 radially self expands outward to place the valve leaflets 210, 212 in the tilted configuration. In addition, the second prosthetic valve assembly 200 may include additional or alternative releasable holding member configured to restrain the valve leaflets 210, 212 in the planar configuration. For example, the second support frame portion 214 may be formed of a bioabsorbable material and be configured as a bioabsorbable member configured to the valve leaflets 210, 212 for a desired period of time. Upon bioabsorption of the second support frame portion 214, the first support frame portion 202 radially expands to place the valve leaflets 210, 212 in the tilted configuration. The cartridge may be implanted within a bioabsorbable second support frame portion 214 as shown in FIG. 3A.

In one aspect, a first support frame portion 202 comprises a self-expanding material attached to the first valve leaflet 210, the first support frame portion 202 being configured to urge the first valve leaflet 210 from the planar configuration to the tilted configuration by self-expansion of a portion of the first support frame portion 202 after release of the leaflet holding member (e.g., a bioabsorbable second support frame portion 214 and/or a bioabsorbable thread 223). The holding member resists the self-expansion of the support frame and may include at least one structure selected from the group consisting of: a bioabsorbable suture, a portion of the support frame comprising a bioabsorbable polymer or bioabsorbable metal and a member comprising a bioabsorbable material connecting two portions of the support frame. The leaflet holding member may include one or more bioabsorbable polymers or metals and may be absorbable within a remodeling-effective period of time, such as about 14 days to 60 days after implantation within a blood vessel. For example, the first support frame portion 202 may be formed from a shape memory metal or polymer and the releasable holding member for restraining the valve leaflet may comprise a bioabsorbable polymer or metal.

After a period of time sufficient for both the second support frame portion 214 and the bioabsorbable threads 223 to be absorbed, the first support frame portion 202 moves to a radially expanded configuration shown in FIGS. 3B and 3C thereby placing the valve leaflets in a tilted configuration. In the tilted configuration, the valve leaflets 210, 212 permit fluid flow through the body vessel 204 in a first direction 208 (FIG. 3C), while substantially limiting fluid flow in a second direction 206 (FIG. 3B). The valve leaflets 210, 212 are sufficiently flexible to permit fluctuations in fluid pressure and flow direction to move the orifice 224 between the open configuration in FIG. 3C and the closed configuration in FIG. 3B as a result of fluid contact with the surfaces of the valve leaflets 210, 212. The valve leaflets 210, 212 should be stiff enough to prevent the valve orifice 224 from prolapsing or tearing away from the first support frame portion 202 while resisting fluid flow in the second (antegrade) direction 206. The base 210' of the first valve leaflet and the base 212' of the second valve leaflet 212 are positioned to sealably engage the wall of the body vessel 204 in the tilted configuration, such that fluid flow in the first direction 208 is directed through the valve orifice 224, while fluid flow in the second direction 206 is directed to the volume between the valve leaflet 210, 212 and the wall of the body vessel 204.

Methods of manufacturing implantable medical devices, such as the embodiments described above, are also provided. The medical devices are preferably manufactured as a prosthetic valve for delayed function and in situ remodeling of a portion thereof upon implantation within a body vessel. The method may include the steps of: (a) attaching a valve leaflet including a remodelable material to a support frame defining a lumen for fluid flow and (b) attaching to the support frame a releasable holding member configured to restrain the valve leaflet in the first configuration.

The valve leaflet may be attached to the support frame oriented in a first configuration permitting a bidirectional longitudinal fluid flow past the leaflet in both a first direction along and a second direction opposite the first direction. The valve leaflet attached to the support frame is preferably moveable from the first configuration to a second configuration permitting fluid flow along the longitudinal axis in the first direction while substantially limiting fluid flow through the lumen in the direction opposite the first direction.

The support frame may extend along a longitudinal axis and be configured for implantation within a body vessel. Optionally, the support frame may be self-expandable. A self-expanding support frame may be maintained in a compressed first configuration prior to or after attachment of the remodelable material to the support frame. The support frame may be resistively maintained in the compressed first configuration by the means for restraining the valve leaflet. The releasable leaflet holding member may simultaneously prevent the valve leaflet from moving to the second configuration and the valve leaflet is preferably moveable to the second configuration within the lumen upon removal of the releasable holding member.

In one example, the valve leaflet is a first valve leaflet, and the method may further comprise the step of attaching a second valve leaflet to the support frame. The first valve leaflet and the second valve leaflet may each include a remodelable material and extend from a leaflet base to a leaflet free edge distal to the leaflet base. Furthermore, the first valve leaflet and the second valve leaflet may each be separately attached to the support frame in a substantially planar first configuration oriented substantially parallel to each other along the longitudinal axis, and the first valve leaflet and the second valve leaflet may be in the planar first configuration permitting a bidirectional fluid flow along the longitudinal axis of the support frame in both a first direction and a second direction opposite the first direction. In addition, the first valve leaflet and the second valve leaflet may be moveable from the planar first configuration to a tilted second configuration. The tilted second configuration may include the free edge of the first valve leaflet in contact with the free edge of the second valve leaflet to form at least a portion of a valve orifice, and the base of the first valve leaflet and the base of the second valve leaflet each being positioned a greater distance from the longitudinal axis in the tilted configuration than in the planar configuration. The prosthetic valve assembly in the tilted configuration preferably permits fluid flow along the longitudinal axis of the prosthetic valve assembly in the first direction while substantially limiting fluid flow in the direction opposite the first direction.

The method of manufacturing may also include a step of providing and configuring one or more releasable holding members configured to restrain the valve leaflets in the planar configuration. Preferably, the releasable holding member also prevents each valve leaflet from moving to the tilted configuration. The valve leaflets preferably move to the tilted configuration upon release of the releasable holding member. The support frame is preferably configured to urge the first valve leaflet from the planar configuration to the tilted configuration by self-expansion of a portion of the support frame when the releasable holding member is released. For example, the releasable holding member may include one or more bioabsorbable polymers or metals and is absorbable within about 14 days to 60 days after implantation within a blood vessel. The support frame may be formed from a shape memory metal or polymer and the releasable holding member may include a bioabsorbable polymer or metal.

Remodelable Materials

Remodelable materials can be intraluminally implanted within a body cavity, such as a blood vessel or organ, using percutaneous transcatheter techniques. Non-remodelable materials having an attached material(s) to promote remodeling may also be used and are considered remodelable materials as used herein. The implanted remodelable or non-remodelable materials can be attached to a frame to form a valve or flow modifying device, or can be implanted without a frame. In either case, the materials can be isolated and prepared by various techniques. Any synthetic or natural remodelable material, or combination of remodelable materials, can be used as a remodelable material for practicing the present invention. Combinations of remodelable and non-remodelable materials may also be used. The material may also be non-remodelable material having a modified surface to encourage remodeling thereon. Examples of suitable synthetic materials include polymeric materials such as polyesters, such as poly(ethylene terephthalate), polylactide, polyglycolide and copolymers thereof; fluorinated polymers, such as polytetrafluoroethylene (PTFE), expanded PTFE and poly (vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. These materials may be coated with ligands and the like and can provide a scaffold onto which cellular in-growth can occur, eventually allowing the material to remodel into a structure of host cells.

Naturally derived or synthetic collagen can provide retractable remodelable materials. Naturally derived or synthetic collagenous material, such as extracellular matrix material, is suitable remodelable materials. Examples of remodelable materials include, for instance, submucosa, renal capsule membrane, dura mater, pericardium, serosa, and peritoneum or basement membrane materials. Collagen can be extracted from various structural tissues as is known in the art and reformed into sheets or tubes, or other shapes. The remodelable material may also be made of Type III or Type IV collagens or combinations thereof. U.S. Pat. Nos. 4,950,483, 5,110,064 and 5,024,841 relate to such remodelable collagen materials and are incorporated herein by reference. Further examples of materials useful as remodelable materials include: compositions comprising collagen matrix material, compositions comprising epithelial basement membranes as described in U.S. Pat. No. 6,579,538 to Spievack, the enzymatically digested submucosal gel matrix composition of U.S. Pat. No. 6,444,229 to Voytik-Harbin et al., materials comprising the carboxy-terminated polyester ionomers described in U.S. Pat. No. 5,668,288 to Storey et al., collagen-based matrix structure described in U.S. Pat. No. 6,334,872 to Termin et al., and combinations thereof. In some embodiments, submucosal tissues for use as remodelable materials include intestinal submucosa, stomach submucosa, urinary bladder submucosa, uterine submucosa, cadaveric valves, and umbilical cord sheath or cells therefrom. A specific example of a suitable remodelable material is intestinal submucosal tissue, and more particularly intestinal submucosa delaminated from both the tunica muscularis and at least the tunica mucosa of warm-blooded vertebrate intestine.

One preferred type of remodelable material is extracellular matrix material derived from submucosal tissue, called small intestine submucosa (SIS). Additional information as to submucosa materials useful as ECM materials herein can be found in U.S. Pat. Nos. 4,902,508; 5,554,389; 5,993,844; 6,206,931; 6,099,567; and U.S. Pat. No. 6,375,989, as well as published U.S. Patent Applications US2004/0180042A1 and US2004/137042A1, which are all incorporated herein by reference. For example, the mucosa can also be derived from vertebrate liver tissue as described in WIPO Publication, WO 98/25637, based on PCT application PCT/US97/22727; from gastric mucosa as described in WIPO Publication, WO 98/26291, based on PCT application PCT/US97/22729; from stomach mucosa as described in WIPO Publication, WO 98/25636, based on PCT application PCT/US97/23010; or from urinary bladder mucosa as described in U.S. Pat. No. 5,554,389; the disclosures of all are expressly incorporated herein.

The remodelable material can be isolated from biological tissue by a variety of methods. In general, a remodelable material such as an extracellular matrix (ECM) material can be obtained from a segment of intestine that is first subjected to abrasion using a longitudinal wiping motion to remove both the outer layers (particularly the tunica serosa and the tunica muscularis) and the inner layers (the luminal portions of the tunica mucosa). Typically the SIS is rinsed with saline and optionally stored in a hydrated or dehydrated state until use as described below. The resulting submucosa tissue typically has a thickness of about 100-200 micrometers, and may consist primarily (greater than 98%) of acellular, eosinophilic staining (H&E stain) ECM material.

Preferably, the source tissue for the remodelable material is disinfected prior to delamination by using the preparation disclosed in U.S. Pat. No. 6,206,931, filed Aug. 22, 1997 and issued Mar. 27, 2001 to Cook et al., and US Patent Application US2004/0180042A1 by Cook et al., filed Mar. 26, 2004, published Sep. 16, 2004 and incorporated herein by reference in its entirety. Most preferably, the tunica submucosa of porcine small intestine is processed in this manner to obtain the ECM material. This method is believed to substantially preserve the aseptic state of the tela submucosa layer, particularly if the delamination process occurs under sterile conditions. Specifically, disinfecting the tela submucosa source, followed by removal of a purified matrix including the tela submucosa, e.g. by delaminating the tela submucosa from the tunica muscularis and the tunica mucosa, minimizes the exposure of the tela submucosa to bacteria and other contaminants. In turn, this enables minimizing exposure of the isolated tela submucosa matrix to disinfectants or sterilants if desired, thus substantially preserving the inherent biochemistry of the tela submucosa and many of the tela submucosa's beneficial effects.

An alternative to the preferred method of ECM material isolation comprises rinsing the delaminated biological tissue in saline and soaking it in an antimicrobial agent, for example as disclosed in U.S. Pat. No. 4,956,178. While such techniques can optionally be practiced to isolate ECM material from submucosa, preferred processes avoid the use of antimicrobial agents and the like which may not only affect the biochemistry of the matrix but also can be unnecessarily introduced into the tissues of the patient. Other disclosures of methods for the isolation of ECM materials include the preparation of intestinal submucosa described in U.S. Pat. No. 4,902,508, the disclosure of which is incorporated herein by reference. Urinary bladder submucosa and its preparation is described in U.S. Pat. No. 5,554,389, the disclosure of which is incorporated herein by reference. Stomach submucosa has also been obtained and characterized using similar tissue processing techniques, for example as described in U.S. patent application Ser. No. 60/032,683 titled STOMACH SUBMUCOSA DERIVED TISSUE GRAFT, filed on Dec. 10, 1996, which is also incorporated herein by reference in its entirety. (U.S. Pat. No. 6,099,567 claims priority to U.S. provisional application 60/032,683.)

Bioabsorbable Releasable Holding Member

As described with reference to the prosthetic valve assemblies above, some embodiments may include a bioabsorbable releasable holding member that may have any suitable configuration adapted to maintain a remodelable material and/or valve leaflet in a desired configuration for a desired period of time upon implantation of the prosthetic valve assembly within a body vessel. Preferably, the prosthetic valve assembly is configured to maintain the remodelable material and/or valve leaflet in a second configuration after release of the leaflet holding member, releasing the leaflet from the first configuration. The first configuration may be selected to permit remodeling of the remodelable material within a body vessel for a desired period of time. This time period is preferably selected to be an effective period of time for remodeling of the remodelable material to occur in situ, and may be selected by the material and structure of the bioabsorbable restraining means. A prosthetic valve device that maintains the remodelable material in a first configuration for a shorter period of time may be obtained by selecting a bioabsorbable restraining means that is quickly dissipated by bioabsorption or break down upon implantation within a body vessel. Conversely, a prosthetic valve device that maintains the remodelable material in a first configuration for a longer period of time may be obtained by selecting a releasable holding member that is more slowly dissipated by bioabsorption or break down upon implantation within a body vessel. While two examples of the bioabsorbable releasable holding member include a bioabsorbable frame portion and a bioabsorbable thread illustrated above, any suitable structure (including combinations of a bioabsorbable frame portion and a bioabsorbable thread) may be used. It is also possible to have a portion of the releasable holding means that is bioabsorbable and another portion that is not bioabsorbable where the combination allows for release of the holding member. For example, the bioabsorbable releasable holding member may include at least one structure selected from the following: a bioabsorbable suture, a portion of the support frame comprising a bioabsorbable polymer or metal and a member comprising a bioabsorbable material connecting two portions of the support frame. The support frame may include a self-expanding material configured to move the valve leaflet from the first configuration to the second configuration after release of the leaflet holding member.

In one aspect, the bioabsorbable releasable holding member comprises a polymer, such as a bioabsorbable elastomer. The bioabsorbable elastomer is preferably a polymer selected to provide a mechanically stable means for restraining a remodelable material and/or valve leaflet (e.g., a valve leaflet comprising a remodelable material) in a desired position for a desired period of time sufficient to permit a desired degree of remodeling of the remodelable material in situ within a body vessel. The bioabsorbable elastomer can include a hydrogel, an elastin-like peptide, a polyhydroxyalkanoates (PHA), polyhydroxybutyrate compounds, or combinations thereof. The bioabsorbable elastomer can be selected based on various design criteria, including the desired rate of release of the therapeutic agent and the degradation mechanism. In some embodiments, the bioabsorbable elastomer comprises one or more hydrolyzable chemical bonds, such as an ester, a desired degree of crosslinking, a degradation mechanism with minimal heterogeneous degradation, and nontoxic monomers.

The bioabsorbable elastomer may be a polyhydroxyalkanoate compound, a hydrogel, poly(glycerol-sebacate) or an elastin-like peptide. Desirably, the bioabsorbable elastomer includes a polyhydroxyalkanoate bioabsorbable polymer such as polylactic acid (poly lactide), polyglycolic acid (poly glycolide), polylactic glycolic acid (poly lactide-co-glycolide), poly-4-hydroxybutyrate, or a combination of any of these. Preferably, the therapeutic agent is initially enclosed by the coating or other portions of the medical device, and does not form a portion of the external surface area of the medical device prior to release of the therapeutic agent.

Desirably, the bioabsorbable elastomer comprises a poly-α-hydroxy acid, such as polylactic acid (PLA). PLA can be a mixture of enantiomers typically referred to as poly-D,L-lactic acid. Alternatively, the bioabsorbable elastomer is poly-L(+)-lactic acid (PLLA) or pol-D(−)-lactic acid (PDLA), which differ from each other in their rate of biodegradation. PLLA is semicrystalline. In contrast, PDLA is amorphous, which can promote the homogeneous dispersion of an active species. Unless otherwise specified, recitation of "PLA" herein refers to a bioabsorbable polymer selected from the group consisting of: PLA, PLLA and PDLA. Preferably, the molecular weight of the bioabsorbable elastomer is about 50-500 kDa, more preferably about 60-250 kDa, and most preferably about 75-120 kDa.

The bioabsorbable elastomer can also desirably comprise polyglycolic acid (PGA). Polyglycolic acid is a simple aliphatic polyester that has a semi-crystalline structure, fully degrades in 3 months, and can undergo strength loss within about 1 month after implantation in the body. Compared with PLA, PGA is a stronger acid and is more hydrophilic, and thus more susceptible to hydrolysis. PLA is generally more hydrophobic than PGA, and undergoes a complete mass loss in 1 to 2 years.

The bioabsorbable elastomer can also be a polylactic glycolic acid (PLGA), or other copolymers of PLA and PGA. The properties of the copolymers can be controlled by varying the ratio of PLA to PGA. For example, copolymers with high PLA to PGA ratios generally degrade slower than those with high PGA to PLA ratios. PLGA degrades slightly faster than PLA. The process of lactic acid hydrolysis can be slower than for the glycolic acid units of the PLGA co-polymer. Therefore, by increasing the PLA:PGA ratio in a PLGA co-polymer generally results in a slower rate of in vivo bioabsorption of a PLGA polymer.

A summary of the properties of some desirable bioabsorbable elastomer polymers are shown below in Table 2.

TABLE 1

| Polymer | Crystallinity | Degradation Rate (depends on molecular weight of polymer) | Typical Applications |
| --- | --- | --- | --- |
| PGA | High Crystallinity | 2-3 months | Suture, soft anaplerosis |
| PLLA | Semi-crystalline | >2 years | Fracture fixation, ligament |
| PDLA | Amorphous | 12-16 months | Drug delivery system |
| PLGA | Amorphous | 1-6 months (depends on ratio of LA to GA) | Suture, fracture fixation, oral implant, drug delivery |

The releasable holding member may also be formed from synthetic materials, including, but not limited to polymeric bioabsorbable materials and metallic bioresorable materials. The releasable holding member may also be formed from collagen base structures that may be crossed-linked to control the time until the releasable holding means is released to move the leaflet(s) to the second configuration. One skilled in the art would be able to select a collagenous material with the requisite strength to function as a holding means without undue experimentation (e.g., a multilaminate sheet construct that has been partially fixed with glutaraldehyde to slow degradation).

Remodeling of Implanted Medical Devices

The implanted medical device comprising a remodelable material is preferably permitted to remodel in a first configuration for a desired period of time. This may occur outside the body vessel prior to implantation, but preferably occurs within a body vessel after implantation. The first configuration preferably maintains a valve leaflet comprising a remodelable material a planar configuration. Preferably, the prosthetic valve assembly is configured to maintain a remodelable material, for example as a valve leaflet, in a first configuration without contacting a wall of a body vessel for a first period of time. The first configuration may be maintained within a body vessel, permitting contact of the remodelable material within a body fluid contacting for a first time period while minimizing contact of stagnant fluid with the remodelable material. In the first configuration, the remodelable material is preferably in contact with the fluid flow without being positioned in a manner permitting blood flow to remain in static contact with the remodelable material. For example, the remodelable material in the first configuration may be oriented as a substantially flat sheet parallel to the longitudinal axis of a body vessel, preferably without contacting the wall of the body vessel.

The medical device is configured and adapted to maintain the remodelable material in the first configuration for a period of time effective to remodel at least a portion of the remodelable material by contact with the body fluid. Suitable time periods include 7, 14, 21 and 30 days, as well as 1, 3 and 6 months. For example, the time period may be about 14-90 days. By selecting the configuration and composition of a bioabsorbable restraining means, the time period during which the remodelable material and/or valve leaflets are maintained in the first configuration can be selected. Upon implantation, the remodeling process appears to begin within about 2 days after implantation of a remodelable material such as small intestine submucosa (SIS) and may continue for up to about 90 days, or longer. Without being limited to theory, a number of investigations (discussed below) show that SIS remodeling has been observed on a time scale of about a week to three months in different studies. Accordingly, an implanted medical device can be permitted to remain within a body vessel for the time during the remodeling of SIS. Preferably, the implanted prosthetic medical device is permitted to remain in the body vessel for a time period when the remodeling process can most effectively be preserved, promoted or enhanced. For example, a implanted prosthetic medical device can be permitted to remain in the body vessel for about 6 months, or longer. In one embodiment, the flow-modifying device is provided for about 90 days or longer, or up to about 6 weeks, 4 weeks, or 3 weeks.

In one investigation, researchers implanted a small caliber vascular graft from porcine small intestine submucosa in a canine carotid artery and compared the remodeling process with an autogenous saphenous vein graft implanted in the contralateral carotid artery. At 2 days after implant, the luminal surface of the SIS graft was covered with a thin (30 mu) fibrin meshwork. Smooth muscle cells were observed in the new intima (fibrin meshwork) by 28 days. By 90 days, both types of graft had arterialized with an intima covered by endothelium, a smooth muscle media and marked adventitial fibrosis. Similar histology was observed at 180 days. Sandusky et al., "Histologic findings after in vivo placement of small intestine submucosal vascular grafts and saphenous vein grafts in carotid artery in dogs," *Am. J. Pathol.*, 140(2), 317-24 (February 1992).

In another investigation, SIS venous conduit was implanted between the portal vein and inferior vena cava in Lewis rats. Smooth luminal surface with endothelial-like cells were observed on the implanted SIS material by 3 weeks. Subsequent histology of excised SIS venous grafts demonstrated a confluent luminal endothelial monolayer, absence of thrombus, and neovascularization in the SIS graft. Kim et al., "Small intestinal submucosa as a small-caliber venous graft: a novel model for hepatocyte transplantation on synthetic bioabsorbable polymer scaffolds with direct access to the portal venous system," *J. Pediatr. Surg.*, 34(1), 124-128 (January 1999).

Another study found that SIS vascular grafts explanted after about 60-days were found to be encased in fibrous tissue. Measurements of mechanical properties (compliance, elastic modulus and burst pressure) of the explanted remodeled grafts approached the mechanical properties of the original vessel, indicating that remodeled tissue on the SIS graft possessed similar mechanical properties. Roeder et al., "Mechanical remodeling of small-intestine submucosa small-diameter vascular grafts—a preliminary report," *Biomed. Instrum. Technol.*, 35(2), 110-120 (March 2001).

A study of SIS implanted in the abdominal wall of dogs and rats over a 2 year period indicated that SIS material appeared fully remodeled by 3 months. After 3 months, the SIS was no longer recognizable and appeared to be replaced by host tissue, including collagenous connective tissue, adipose tissue and bundles of skeletal muscle. Notably, SIS was observed to serve as a scaffold for new skeletal muscle tissue in this study. Badylak et al., "Morphologic Study of Small Intestinal Submucosa as a Body Wall Repair Device," *J. Surg. Research*, 103, 190-202 (April 2002).

Another study of square stent-based bicuspid venous valves comprising small intestinal submucosa implanted in the venae cavae of adult sheep for 5 weeks showed remodeling of the SIS material. Remodeling was indicated by the presence of newly formed collagen fibers on the SIS, fibroblasts and inflammatory cells penetrating the SIS leaflets, endothelial cells on the surface of the SIS, and neovascularization of the SIS material. Endothelial cells were found on both surfaces of the SIS valve leaflets. Researchers concluded that the SIS-based valve remodeling occurred independently of vessel wall contact by recruitment of cells directly from circulation. Brountzos, et al, "Remodeling of suspended small intestinal submucosa venous valve: an experimental study in sheep to assess the host cells' origin," *J. Vasc. Interv. Radiol.*, 14(3), 349-356 (March 2003). After a desired time period, the prosthetic medical device may be configured to move the valve leaflets and/or remodelable material to a second configuration adapted to regulate the fluid of body fluid contacting the remodelable material. Preferably, the body fluid flow is blood flow across the remodelable material within a body vessel, such as a venous valve or a heart valve. In the second configuration, the remodelable material may change shape, configuration or orientation within the body vessel to extend across at least a portion of the body vessel and provide a valve function to regulate fluid flow within the body vessel in a substantially unidirectional manner. The remodelable material in the second configuration be configured as one or more valve leaflets forming a heart valve or venous valve.

Frame Materials

The frame of the prosthetic valve may be self-expandable or mechanically expandable. Suitable support frames can be made from a variety of materials and need only be biocompatible or able to be made biocompatible. Examples of suitable materials include, without limitation, stainless steel, nickel titanium (NiTi) alloys, e.g., nitinol, other shape memory and/or superelastic materials, molybdenum alloys, tantalum alloys, titanium alloys, precious metal alloys, nickel chromium alloys, cobalt chromium alloys, nickel cobalt chromium alloys, nickel cobalt chromium molybdenum alloys, nickel titanium chromium alloys, linear elastic Nitinol wires, polymers, and composite materials.

Stainless steel and nitinol are currently considered desirable materials for use in the support frame due at least to their biocompatibility, shapeability, and well-characterized nature. Also, cold drawn cobalt chromium alloys, such as ASTM F562 and ASTM F1058 (commercial examples of which include MP35N™ and Elgiloy™, both of which are available from Fort Wayne Metals, Fort Wayne, Ind.; MP35N is a registered trademark of SPS Technologies, Inc. (Jenkintown, Pa., USA); Elgiloy is a registered trademark of Combined Metals of Chicago LLC (Elk Grove Village, Ill., USA)), are currently considered advantageous materials for the support frame at least because they are non-magnetic materials that provide beneficial magnetic resonance imaging (MRI) compatability, and avoid MRI artifacts typically associated with some other materials, such as stainless steel.

In some embodiments, the frame itself, or any portion of the frame, can include one or more metallic bioabsorbable materials. Suitable metallic bioabsorbable materials include magnesium, titanium, zirconium, niobium, tantalum, zinc and silicon and mixtures and alloys. For example, a zinc-titanium alloy such as discussed in U.S. Pat. No. 6,287,332 to Bolz et al., which is incorporated herein by reference in its entirety, can be used. The metallic bioabsorbable material can further contain lithium, sodium, potassium, calcium, iron and manganese or mixtures thereof. For example, an alloy containing lithium:magnesium or sodium:magnesium can be used. The physical properties of the frame can be controlled by the selection of the metallic bioabsorbable material, or by forming alloys of two or more metallic bioabsorbable materials. For example, when 0.1% to 1%, percentage by weight, titanium is added to zinc, the brittle quality of crystalline zinc can be reduced. In another embodiment, when 0.1% to 2%, percentage by weight, gold is added to a zinc-titanium alloy, the grain size of the material is reduced upon curing and the tensile strength of the material increases.

Percutaneous Medical Device Delivery

A prosthetic valve assembly or components thereof are preferably delivered from a percutaneous catheter within a body vessel. The entire prosthetic valve assembly may be delivered as a single device (e.g., FIGS. 1A, 1B, 2A and 2B), or as two or more separate components, such as the second support frame portion 214 being implanted within a body vessel independently from the cartridge (first support frame portion 202, valve leaflets 210, 212 and bioabsorbable thread 223) shown in FIGS. 3A, 3B and 3C. In either case, the prosthetic valve assembly or components thereof is preferably adapted for transcatheter percutaneous delivery, and can be moveable from a compressed delivery state suitable for introduction to a point of treatment with a catheter delivery system, to a radially expanded implanted state for retention within the body vessel at a point of treatment therein.

Radially expandable support frames include self-expandable or mechanically expandable, (e.g. balloon expandable)

frames. For example, in the peripheral vasculature, vessels are generally more compliant and typically experience dramatic changes in their cross-sectional shape during routine activity. Medical devices for implantation in the peripheral vasculature should retain a degree of flexibility to accommodate these changes of the vasculature. Accordingly, support frames intended for implantation in the peripheral vasculature, such as prosthetic venous valves, advantageously include a self-expandable support frame. These support frames may be more flexible than balloon-expandable support frames following deployment.

Methods of providing a prosthetic valve with delayed function and in situ remodeling of a portion thereof are provided. Such methods may include the steps of: (a) implanting a prosthetic assembly at a point of treatment within a body vessel, the body vessel having a longitudinal axis at a point of treatment, the prosthetic assembly comprising a substantially planar sheet of remodelable material attached to a support frame and a bioabsorbable means for maintaining the remodelable material within the body vessel without contacting the wall of the body vessel, the implanted prosthetic assembly permitting bidirectional fluid flow through the body vessel and in contact with the valve leaflet at the point of treatment; (b) maintaining the prosthetic valve at the point of treatment for a period of time effective for an in situ remodeling of the remodelable material and a bioabsorption of the bioabsorbable means for maintaining the remodelable material within the body vessel, the remodelable material forming a valve leaflet contacting a portion of the body vessel upon bioabsorption of the bioabsorbable means for maintaining the remodelable material within the body vessel; and (c) regulating fluid flow within the body vessel after the bioabsorption of the bioabsorbable means for maintaining the remodelable material within the body vessel by movement of the valve leaflet to permit fluid flow along the longitudinal axis in a first direction, while substantially limiting fluid flow in the opposite direction by movement of the valve leaflet within the body vessel. While many preferred embodiments discussed herein discuss implantation of a medical device in a vein, other embodiments provide for implantation within other body vessels. In another matter of terminology there are many types of body canals, blood vessels, ducts, tubes and other body passages, and the term "vessel" is meant to include all such passages.

Medical devices can be delivered into a body lumen using a system which includes a catheter. In some embodiments, medical devices can be intraluminally delivered inside the body by a catheter that supports the medical device in a compacted form as it is transported to the desired site, for example within a body vessel. Upon reaching the site, the medical device can be expanded and securably placed within the body vessel, for example by securably engaging the walls of the body vessel lumen. The expansion mechanism may involve forcing the support frame to expand radially outward, for example, by inflation of a balloon formed in the distal portion of the catheter, to inelastically deform the support frame and fix it at a predetermined expanded position in contact with the lumen wall. The expansion balloon can then be deflated and the catheter removed. In another technique, the medical device is formed of an elastic material that will self-expand after being compacted. During introduction into the body, the medical device is restrained in the compacted condition. When the support frame has been delivered to the desired site for implantation, the restraint is removed, allowing the medical device to self-expand by its own internal elastic restoring force. Once the medical device is located at the constricted portion of the lumen, the sheath is removed to expose the frame, which is expanded so it contacts the lumen wall. The catheter is subsequently removed from the body by pulling it in the proximal direction, through the larger lumen diameter created by the expanded prosthesis, which is left in the body. An appropriately sized delivery catheter can be selected by one skilled in the art for a given application. For example, some embodiments can be delivered using a delivery catheter selected from one or more delivery catheter sizes from the group consisting of: 3, 4, 5, 6, 7, 8, 9, 10, 11, 12, 13, 14, 15, 16, 17, 18, 19, 20, 21, 22, 23, and 24 French (F) delivery catheters, or increments of 0.1 F therebetween. In some embodiments, a delivery catheter sized between 3F and 24F, or preferably between about 6F and 16F can be used.

In some embodiments, the medical devices or support frame portions thereof impart a radially outward-directed force during deployment, whether self-expanding or radially-expandable. The radially outward directed force can serve to hold the body lumen open against a force directed radially inward, as well as preventing restriction of the passageway through the lumen by intimal flaps or dissections generated by, such as prior balloon angioplasty. Another function of the radially outward directed force can also fix the position of the frame within the body lumen by intimate contact between the frame and the walls of the lumen. Preferably, the outwardly directed forces do not traumatize the lumen walls.

In some embodiments, the delivery catheter can also provide for measurement of a distance within the body vessel lumen. For example, the delivery device and/or a delivery catheter can provide indicia or signals relating to the location or orientation of the remodelable material within the body vessel, or the distance traveled along a body vessel lumen. The means for orienting the frame within a body lumen can correspond to a radiopaque region of the implantable device and/or the means for delivering the device (e.g., a catheter). For example, the radiopaque region can comprise a frame with a marker region, or a delivery device comprising the frame can provide indicia relating to the orientation of the frame within the body vessel. The marker can be a radiopaque portion of the frame detectable by imaging methods including X-ray, ultrasound, Magnetic Resonance Imaging and the like, or by detecting a signal from or corresponding to the marker. In other embodiments, the delivery device can comprise a frame with indicia relating to the orientation of the frame within the body vessel. In other embodiments, indicia can be located, for example, on a portion of a delivery catheter that can be correlated to the location of the frame within a body vessel. The addition of radiopacifiers (i.e., radiopaque materials) to facilitate tracking and positioning of the medical device may be added in any fabrication method or absorbed into or sprayed onto the surface of part or all of the medical device. The degree of radiopacity contrast can be altered by implant content. Radiopacity may be imparted by covalently binding iodine to the polymer monomeric building blocks of the elements of the implant. Common radiopaque materials include barium sulfate, bismuth subcarbonate, and zirconium dioxide. Other radiopaque elements include: cadmium, tungsten, gold, tantalum, bismuth, platinum, iridium, and rhodium. In one preferred embodiment, iodine may be employed for its radiopacity and antimicrobial properties. Radiopacity is typically determined by fluoroscope or x-ray film. Radiopaque, physiologically compatible materials include metals and alloys selected from the Platinum Group metals, especially platinum, rhodium, palladium, rhenium, as well as tungsten, gold, silver, tantalum, and alloys of these metals. These metals have significant radiopacity and in their alloys may be tailored to accomplish an appropriate blend of flexibility and stiffness. They are also largely biocompatible.

Highly preferred is a platinum/tungsten alloy, e.g., 8% tungsten and the remainder platinum. The particular form and choice of material used for the implantable frame will depend on the desired application.

The medical devices can be placed in any medically appropriate location for a given application. For example, in some embodiments, the medical device can serve as part of a venous valve prosthetic and be implanted in the femoral vein, including at the proximal (groin), mid (mid section) or distal (adjacent to the knee) portions of the vein.

The methods and devices described herein are useful in treating a variety of medical conditions, including methods of treating conditions related to undesirable levels of retrograde fluid flow across a valve within a body cavity, such as venous valve related condition. A "venous valve-related condition" is any condition presenting symptoms that can be diagnostically associated with improper function of one or more venous valves. In mammalian veins, venous valves are positioned along the length of the vessel in the form of leaflets disposed annularly along the inside wall of the vein which open to permit blood flow toward the heart and close to prevent back flow. These venous valves open to permit the flow of fluid in the desired direction, and close upon a change in pressure, respiratory rate or calf muscle function. When blood flows through the vein, the pressure forces the valve leaflets apart as they flex in the direction of blood flow and move towards the inside wall of the vessel, creating an opening therebetween for blood flow. The leaflets, however, do not normally bend in the opposite direction and therefore return to a closed position to restrict or prevent blood flow in the opposite, i.e. retrograde, direction after the pressure is relieved. The leaflets, when functioning properly, extend radially inwardly toward one another such that the tips contact each other to block backflow of blood. Two examples of venous valve-related conditions are chronic venous insufficiency and varicose veins.

In the condition of venous valve insufficiency, the valve leaflets do not function properly. For example, the vein can be too large in relation to the leaflets so that the leaflets cannot come into adequate contact to prevent backflow (primary venous valve insufficiency), or as a result of clotting within the vein that thickens the leaflets (secondary venous valve insufficiency). Incompetent venous valves can result in symptoms such as swelling and varicose veins, causing great discomfort and pain to the patient. If left untreated, venous valve insufficiency can result in excessive retrograde venous blood flow through incompetent venous valves, which can cause venous stasis ulcers of the skin and subcutaneous tissue. Venous valve insufficiency can occur, for example, in the superficial venous system, such as the saphenous veins in the leg, or in the deep venous system, such as the femoral and popliteal veins extending along the back of the knee to the groin.

The methods described herein can provide methods of treating such conditions, by reducing or eliminating retrograde fluid flow across a valve within a body vessel. In one aspect, the method can include implanting an occluding device to block an aperture in a native or prosthetic valve within a body vessel. In another aspect, the method can include modifying a valve orifice and/or an aperture in the valve.

The invention includes other embodiments within the scope of the claims, and variations of all embodiments, and is limited only by the claims made by the Applicants.

We claim:

1. A prosthetic valve assembly comprising:
   a. a support frame defining a lumen extending from a proximal end to a distal end along a longitudinal axis and being configured for implantation within a body vessel;
   b. a valve leaflet including a remodelable material, the valve leaflet being attached to the support frame and oriented in a first configuration within the lumen permitting a bidirectional fluid flow through the lumen in a first direction along the longitudinal axis and a second direction opposite the first direction, the valve leaflet being moveable from the first configuration to a second configuration permitting fluid flow through the lumen in the first direction while substantially limiting fluid flow through the lumen in the direction opposite the first direction; and
   c. a releasable holding member configured to restrain the valve leaflet in the first configuration and to prevent the valve leaflet from moving to the second configuration; the valve leaflet being moveable to the second configuration within the lumen upon release of the holding member.

2. The prosthetic valve assembly of claim 1 wherein the releasable holding member is bioabsorbable.

3. The prosthetic valve assembly of claim 2, where the bioabsorbable holding member comprises a bioabsorbable polymer.

4. The prosthetic valve assembly of claim 1 wherein the releasable holding member comprises a metallic releasable holding member.

5. The prosthetic valve assembly of claim 2, where the bioabsorbable holding member includes at least one structure selected from the group consisting of: a bioabsorbable suture, a portion of the support frame comprising a bioabsorbable polymer and a member comprising a bioabsorbable material connecting two portions of the support frame.

6. The prosthetic valve assembly of claim 1, wherein the support frame comprises a self-expanding material configured to move the valve leaflet from the first configuration to the second configuration upon release of the holding member.

7. The prosthetic valve assembly of claim 1, wherein the valve leaflet in the first configuration is substantially parallel to the longitudinal axis.

8. The prosthetic valve assembly of claim 7, wherein the valve leaflet in the first configuration is configured as a substantially flat sheet contained within the lumen defined by the support frame.

9. The prosthetic valve assembly of claim 8, wherein the valve leaflet in the second configuration extends from a base portion contacting a portion of the support frame to a free edge portion distal to the base portion, the free edge being flexibly moveable within the lumen to define at least a portion of a valve orifice moveable therein to permit the fluid flow through the lumen in the first direction while substantially limiting fluid flow through the lumen in the direction opposite the first direction.

10. The prosthetic valve assembly of claim 2, wherein bioabsorbable holding member comprises one or more bioabsorbable polymers or metals and is absorbable within about 14 days to 60 days after implantation within a blood vessel.

11. The prosthetic valve assembly of claim 10, wherein
   a. the bioabsorbable holding member includes at least one structure selected from the group consisting of: a bioabsorbable suture, a portion of the support frame comprising a bioabsorbable polymer and a member comprising a bioabsorbable material connecting two portions of the support frame; and b. the support frame comprises a self-expanding material configured to move the valve leaflet from the first configuration to the second configuration upon release of the holding member.

12. A prosthetic valve assembly comprising:
a. a self-expandable support frame configured for implantation within a body vessel, the support frame having a longitudinal axis and being adapted to permit fluid flow along the longitudinal axis;
b. a first valve leaflet and a second valve leaflet each including a remodelable material and extending from a leaflet base to a leaflet free edge distal to the leaflet base,
   i. the first valve leaflet and the second valve leaflet each being separately attached to the support frame in a substantially planar configuration oriented substantially parallel to each other along the longitudinal axis, the first valve leaflet and the second valve leaflet in the substantially parallel configuration permitting a bidirectional fluid flow along the longitudinal axis of the support frame in both a first direction and a second direction opposite the first direction;
   ii. the first valve leaflet and the second valve leaflet being moveable from the planar configuration to a tilted configuration, the tilted configuration having the free edge of the first valve leaflet contact the free edge of the second valve leaflet to form at least a portion of a valve orifice, and the base of the first valve leaflet and the base of the second valve leaflet each being positioned a greater distance from the longitudinal axis in the tilted configuration than in the planar configuration; the prosthetic valve assembly in the tilted configuration permitting fluid flow along the longitudinal axis in the first direction while substantially limiting fluid flow in the direction opposite the first direction; and
c. a releasable holding member configured to restrain the valve leaflets in the planar configuration and to simultaneously preventing each valve leaflet from moving to the tilted configuration; the valve leaflets being moveable to the tilted configuration upon release of the holding member.

13. The prosthetic valve assembly of claim 12 wherein the releasable holding member is bioabsorbable.

14. The prosthetic valve assembly of claim 12, where the support frame comprises a self-expanding material attached to the first valve leaflet, the support frame being configured to urge the first valve leaflet from the planar configuration to the tilted configuration by self-expansion of a portion of the support frame upon release of the holding member.

15. The prosthetic valve assembly of claim 13, where the bioabsorbable holding member resists the self-expansion of the support frame and includes at least one structure selected from the group consisting of: a bioabsorbable suture, a portion of the support frame comprising a bioabsorbable polymer and a member comprising a bioabsorbable material connecting two portions of the support frame.

16. The prosthetic valve assembly of claim 13, wherein the bioabsorbable holding member comprises one or more bioabsorbable polymers or metals and is absorbable within about 14 days to 60 days after implantation within a blood vessel.

17. The prosthetic valve assembly of claim 12, wherein the support frame is a shape memory material and the holding member comprises a bioabsorbable polymer or metal.

* * * * *